(12) United States Patent
Lazarev

(10) Patent No.: US 8,552,179 B2
(45) Date of Patent: Oct. 8, 2013

(54) ORGANIC COMPOUND, PHOTOVOLTAIC LAYER AND ORGANIC PHOTOVOLTAIC DEVICE

(75) Inventor: Pavel I. Lazarev, London (GB)

(73) Assignee: Cryscade Solar Ltd, Nicosia (CY)

( * ) Notice: Subject to any disclaimer, the term of this patent is extended or adjusted under 35 U.S.C. 154(b) by 878 days.

(21) Appl. No.: 12/442,469

(22) PCT Filed: Sep. 26, 2007

(86) PCT No.: PCT/GB2007/050583
§ 371 (c)(1),
(2), (4) Date: Mar. 23, 2009

(87) PCT Pub. No.: WO2008/038047
PCT Pub. Date: Apr. 3, 2008

(65) Prior Publication Data
US 2010/0065122 A1    Mar. 18, 2010

(30) Foreign Application Priority Data

Sep. 26, 2006  (GB) ................................. 0618955.9
Apr. 3, 2007   (GB) ................................. 0706514.7

(51) Int. Cl.
*C07B 47/00*    (2006.01)
*C07D 471/00*   (2006.01)
*C07D 221/18*   (2006.01)
*H01L 31/00*    (2006.01)

(52) U.S. Cl.
USPC ............... 540/145; 546/37; 546/38; 136/252; 136/256; 136/263

(58) Field of Classification Search
USPC ........ 540/145; 546/37, 38; 136/263, 252, 256
See application file for complete search history.

(56) References Cited

U.S. PATENT DOCUMENTS

2002/0137925 A1 * 9/2002 Lindsey et al. ............... 540/145

OTHER PUBLICATIONS

Kelly et al. [J. Am. Chem. Soc. 128, 4779-4791(2006)].*
You et al. [Organic Letters 6(14), 2401-2404(2004)].*
Jingzhi et al. [Chinese Science Bulletin 50(19), 2157-2160(2005)].*
Wu et al. [Wuli Xuebao, 53(5), 1604-1610(2004)].*
Kirmaier et al. [J. Phys. Chem. B 107, 3443-3454(2003)].*
Xiao et al. [J. Phys. Chem. B 109, 3658-3667 (2005)].*

* cited by examiner

*Primary Examiner* — Ling Choi
*Assistant Examiner* — Monique Peets
(74) *Attorney, Agent, or Firm* — Houst Consulting

(57) ABSTRACT

The present invention relates generally to the field of organic chemistry and particularly to the organic compound for organic photovoltaic devices. More specifically, the present invention is related to the organic compounds and the organic photovoltaic devices based on these compounds. In one preferred embodiment, this organic compound has the general structural formula (I) where $Het_1$ is a predominantly planar polycyclic molecular system of first type; $Het_2$ is a predominantly planar polycyclic molecular system of second type; A is a bridging group providing a lateral bond of the molecular system $Het_1$ with the molecular system $Het_2$ via strong chemical bonds; n is 1, 2, 3, 4, 5, 6, 7 or 8; B1 and B2 are binding groups; i is 0, 1, 2, 3, 4, 5, 6, 7 or 8; j is 0, 1, 2, 3, 4, 5, 6, 7 or 8; S1 and S2 are groups providing solubility of the organic compound; k is 0, 1, 2, 3, 4, 5, 6, 7 or 8; m is 0, 1, 2, 3, 4, 5, 6, 7 or 8; D1 and D2 are substituents independently selected from a list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$; y is 0, 1, 2, 3, 4, 5, 6, 7 or 8; and z is 0, 1, 2, 3, 4, 5, 6, 7 or 8. Said organic compound absorbs electromagnetic radiation in at least one predetermined spectral subrange within a wavelength range from 400 to 3000 nm and is capable to form supramolecules. The molecular system $Het_1$, the bridging group A, and the molecular system $Het_2$ are capable to form a donor-bridge-acceptor system providing dissociation of excited electron-hole pairs. A solution of the organic compound or its salt is capable of forming a solid photovoltaic layer on a substrate.

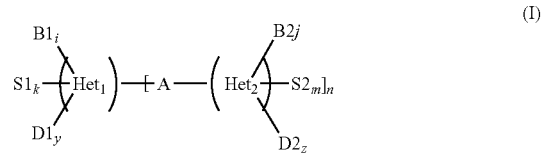

(I)

16 Claims, 25 Drawing Sheets

ORGANIC COMPOUND, PHOTOVOLTAIC LAYER AND ORGANIC PHOTOVOLTAIC DEVICE

The present invention relates generally to organic compounds, organic photovoltaic layer based on such compounds and organic photovoltaic devices intended for transforming light and, specifically, for converting solar energy into electric energy.

Photovoltaic devices are intended for converting electromagnetic radiation into electricity. Such devices are used to drive power consuming loads so as to provide, for example, lighting or heating, or to operate electronic equipment. Thereby, an electronic device (e.g., a computer monitor, display, exposure meter, etc.) connected as the external resistive load to a photovoltaic source can operate using converted solar energy. Such power generation applications often involve the charging of batteries or other energy storage devices, so that equipment operation may continue when direct illumination from the sun or other ambient light source is no longer available. As used herein, the term "resistive load" refers to any power consuming or storing device, equipment, or system.

Photovoltaic devices produce a photogenerated built-in voltage when they are connected to a resistive load and are irradiated by light. When irradiated without any external resistive load, a photovoltaic device generates its maximum possible built-in voltage V called open-circuit voltage (Voc). If a photovoltaic device is irradiated with its electrical contacts shorted, a maximum current I called short-circuit current (Isc), is produced. When actually used to generate power, a photovoltaic device is connected to a finite resistive load and the output power is given by the product of the current and voltage, I×V. The maximum total power generated by a photovoltaic device is inherently incapable of exceeding the product Isc×Voc. When the load value is optimized for maximum power extraction, the current and voltage have values Imax and Vmax, respectively.

The estimation of conversion efficiency of a photovoltaic device is the fill factor, ff, defined as $$ff = (Imax \cdot Vmax)/(Isc \cdot Voc),$$

where ff is always less than unity, as Isc and Voc are never obtained simultaneously in real practice. Nevertheless, as ff approaches unity, the device is more efficient.

Other criteria of the efficiency of a photovoltaic device can be used as well. In particular, the external quantum efficiency characterizes the number of electrons generated per one incident radiation quantum (photon) and the internal quantum efficiency is the number of electrons produced per one photon absorbed by the given photovoltaic device.

It is similarly possible to give definitions of efficiency for other photosensitive optoelectronic devices.

There were numerous attempts at reducing the cost of production of photosensitive optoelectronic devices, including solar cells. Organic photoconductors and organic semiconductors were considered as candidate materials because of the option to produce organic films by deposition from solutions or by other low-cost techniques. However, the conversion efficiency of solar cells employing such organic materials was always less than the conversion efficiency of conventional solar cells based on inorganic materials. Practical on-ground applications require greater values of the photovoltaic conversion efficiency.

When electromagnetic radiation of an appropriate energy is incident upon a semiconducting organic material, for example, an organic molecular crystal, a photon can be absorbed to produce an excited molecular state. This is represented symbolically as $S0 + h\nu \Rightarrow S0^*$, where $S0$ and $S0^*$ denote ground and excited molecular states, respectively. This energy absorption is associated with the transition of an electron from a bound state in the highest occupied molecular orbital (HOMO), which may be a $\pi$ bond, to the lowest unoccupied molecular orbital (LUMO), which may be a $\pi^*$ bond, or equivalently, the transition of a hole from the LUMO to the HOMO. In organic photoconductor layers, the generated molecular state is generally believed to be an exciton. Exciton is an elementary electrically neutral excitation possessing a quasiparticle character in semiconductors. In organic semiconductors, excitons appears upon the formation of electron-hole pairs following the HOMO-LUMO transition. If the photoexcitation energy is smaller than the HOMO-LUMO energy difference, the electron and hole cannot independently move in the semiconductor material and occur in the bound state, representing an electrically neutral quasiparticle (exciton). Travelling in a semiconductor material, excitons can transfer the energy. The excitons can exist for an appreciable time (lifetime) before exhibiting geminate recombination, which refers to the process of the original electron and hole recombination with each other, as opposed to recombination with holes or electrons from other pairs. Thus, the process of photon absorption in organic semiconductors leads to the creation of bound electron-hole pairs (excitons). The excitons can diffuse toward the so-called dissociation centers, where the positive and negative charges can separate. Such dissociation can be realized, for example, at a boundary (interface) of two organic layers made of different organic materials, provided that one of these materials has a greater electron affinity (EA) and the other possesses a lower ionization potential (IP). The material of higher EA can accept electrons from the conduction band of the other material and is called electron acceptor. The material possessing a lower ionization potential can accept holes from the valence band of the organic semiconductor in contact, the former material is called the hole acceptor or the electron donor, because it can also donate electrons to an adjacent acceptor. It should be noted that a difference between IP and EA must be sufficiently large so as to overcome the energy of exciton binding (the latter is typically around 0.4 eV). Otherwise excitons do not dissociate (the bound electron-hole pairs do not separate into free charge carriers) and such bound charges eventually recombine at the interface between layers of donor and acceptor materials. Being separated, the charges move toward the corresponding electrodes of the photovoltaic device: holes drifting to the anode and electrons to the cathode, thus creating the electric current. Therefore, in contrast to inorganic semiconductors, where mobile charge carriers are formed directly upon the absorption of light, the mobile charge carriers in the molecular (organic) semiconductors such as porphyrins, perylene derivatives, and tetrapirolic macro-cyclic compounds appear as a result of the decomposition of excitons formed upon light absorption.

The electron-hole pair representing an exciton can be separated in the region of an internal electric field generated in the semiconductor material. To produce such internally generated electric fields occupying a substantial volume, the usual method is to juxtapose two layers of materials with appropriately selected conduction properties, especially with respect to their distribution of molecular quantum energy states. The interface of these two materials is called a photovoltaic heterojunction. In traditional semiconductor theory, materials for forming photovoltaic heterojunctions have been denoted as generally being of either n (donor) or p (acceptor) type. Here, n-type denotes that the majority carrier type is electron.

This could be viewed as the type of materials having many electrons in relatively free energy states. The p-type indicates that the majority carrier type is a hole. Such materials have many holes in relatively free energy states. The type of the background (that is, not photogenerated) majority carrier and their concentration depend primarily on the unintentional doping by defects or impurities. The type and concentration of impurities determine the value of the Fermi energy, or the Fermi level position, within the gap between the lowest unoccupied molecular orbital (LUMO) and the highest occupied molecular orbital (HOMO), called the LUMO-HOMO gap. The Fermi energy characterizes the statistical occupation of molecular quantum energy states, representing the value of energy for which the probability of occupation is equal to 0.5. The Fermi level position near the LUMO energy indicates that electrons are the predominant carrier type. The Fermi energy being close to the HOMO energy indicates that holes are the predominant carriers.

There are the so-called self-assembling solar cells based on a mixture of a crystalline dye and a liquid crystal material. The mixture is capable of self-organizing with the formation of a photovoltaic cell characterized by high photovoltaic conversion efficiency. The liquid crystal component represents an organic compound belonging to hexabenzocoronenes whose disc-shaped molecules are capable of forming a liquid crystal phase at room temperature. These molecules are aggregated into columns (stacks) effectively conducting at room temperature. The dye component represents a perylene dye. A solution of two components in chloroform is applied onto a solid substrate by centrifuging. Then the solvent is evaporated to leave the substrate covered by a self-organizing layer in which the perylene dye is crystallized. The interface between two organic materials features the light-induced charge separation. The quantum efficiency of photovoltaic devices implementing such organic heterojunctions reaches 34%, which implies that each 100 absorbed photons yield on the average 34 electron-hole pairs.

There is a known photovoltaic converter based on a MEH-PPV copolymer and a perylene derivative (PPEI) (see J. J. Dittmer et al., Synthetic Metals, Vol. 102, 879-880 (1999)). In this system, MEH-PPV acts as a hole acceptor and PPEI, as the electron acceptor (hole donor). Excitons photogenerated in the organic semiconductor subsequently decay into free charge carriers (electrons and holes) at the interface between the donor and acceptor components. The introduction of PPEI significantly increases the external quantum efficiency of photovoltaic devices employing this system. The PPEI particles are distributed in the MEH-PPV matrix volume over a distance equal to the exciton diffusion length (~9 nm). In presence of PPEI stimulates charge separation in thin-film MEH-PPV structures.

There is a known photovoltaic cell (Klaus Petritsch, PhD Thesis, "Organic Solar Cell Architectures", Cambridge and Graz, July 2000, Chapter 3, Single Layer Devices, p. 31) based on a Schottky barrier containing the active layer of an organic semiconductor, comprising a rectifying junction with electrode. This organic layer is based on undoped poly(acetylene) and has a thickness approximately equal to the depth of a depleted layer. The electrode contains a thin layer of magnesium known to form a rectifying Schottky barrier in contact with poly(acetylene). The magnesium layer is overcoated with a gold film.

Another known photovoltaic cell (Klaus Petritsch, PhD Thesis, "Organic Solar Cell Architectures", Cambridge and Graz, July 2000, Chapter 4, Double Layer Devices, p. 67) comprises the first layer of an organic electron donor material in contact with the second layer made of an organic electron acceptor material. At least one of these materials is capable of absorbing light in a wavelength range from 350 to 1000 nm and the two materials in contact form a rectifying junction. The cell is provided with electrodes forming Ohmic contacts at least with a part of the surface of organic layers. A distinctive feature of said photovoltaic cell is that the organic materials employed contain organic compounds with generally planar polycyclic nuclei. These compounds are capable of forming a layer structure with a total thickness not exceeding 0.5 micron.

A general disadvantage of the organic materials used in the aforementioned photovoltaic devices consists in the fact that the organic layers of these materials do not have crystalline structure. For this reason, the mobility of electrons and holes in these layers is much lower as compared to that in the same bulk crystalline materials. As a result, electrons and holes do not leave the active region of a semiconductor structure during the exciton lifetime and recombine. Such electron-hole pairs do not contribute to the photocurrent, and the photovoltaic conversion efficiency decreases. In addition, a decrease in the electron and hole mobility leads to an increase in the resistivity of the material and, hence, in the serial resistance of the photovoltaic device. This implies increase of Ohmic losses and additional decrease in the photovoltaic conversion efficiency. Another disadvantage of the aforementioned photovoltaic devices employing organic films without crystalline structure is that these materials are characterized by extremely small diffusion length of photogenerated excitons. This necessitates using photovoltaic structures consisting of very thin layers of thicknesses comparable with the exciton diffusion length, which also decreases both external and internal quantum efficiency of such devices.

It has been shown, that adding a stable radical to the bridge molecule in a donor-bridge-acceptor (D-B-A) system is potentially an important way to control charge- and spin-transfer dynamics through the D-B-A system (see, Erin T. Chernick, Qixi Mi, Richard F. Kelley, Emily A. Weiss, Brooks A. Jones, Tobin J. Marks,* Mark A. Ratner, and Michael R. Wasielewski, "Electron Donor-Bridge-Acceptor Molecules with Bridging Nitronyl Nitroxide Radicals: Influence of a Third Spin on Charge- and Spin-Transfer Dynamics", J. AM. CHEM. SOC. 2006, 128, 4356-4364). Authors of this article have added a nitronyl nitroxide (NN•) stable radical to a D-B-A system having well-defined distances between the components: MeOAn-6ANI-Ph(NN•)-NI, where MeOAn=p-methoxyaniline, 6ANI=4-(N-piperidinyl)-naphthalene-1,8-dicarboximide, Ph=phenyl, and NI=naphthalene-1,8:4,5-bis (dicarboximide). MeOAn-6ANI, NN•, and NI are attached to the 1, 3, and 5 positions of the Ph bridge. Using both time-resolved optical and EPR spectroscopy, the authors show that the NN* influences the spin dynamics of the photogenerated triradical states $^{2,4}$(MeOAn$^+$•-6ANI-Ph(NN•)-NI$^-$•), resulting in slower charge recombination within the triradical compared to the corresponding biradical lacking NN*. The observed spin-spin exchange interaction between the photogenerated radicals MeOAn+• and NI$^-$• is not altered by the presence of NN•, which only accelerates radical pair intersystem crossing. Charge recombination within the triradical results in the formation of $^{2,4}$(MeOAn-6ANI-Ph(NN•)-$^3$*NI), in which NN• is strongly spin-polarized. Normally, the spin dynamics of correlated radical pairs do not produce a net spin polarization; however, net spin polarization appears on NN• with the same time constant as describes the photogenerated radical ion pair decay. This effect is attributed to antiferromagnetic coupling between NN• and the local triplet state $^3$*NI, which is populated following charge recombination. This requires an effective switch in the spin basis set between the triradical and the three-spin charge recombination product having both NN• and $^3$*NI present.

A Donor-Bridge-Acceptor molecule, D-B-A, was synthesized to probe the effects of changing the electronic state of the bridge molecule, B, on the rates of electron transfer within the D-B-A system (see, Ryan T. Hayes, Michael R. Wasielewski, and David Gosztola, "Ultrafast Photoswitched Charge Transmission through the Bridge Molecule in a Donor-Bridge-Acceptor System", *J. Am. Chem. Soc.* 2000, 122, 5563-5567). Selective photoexcitation of D in a tetrahydrofuran solution of D-B-A with 400 nm, 130 fs laser pulses at t=0 ps results in photoinduced electron transfer to yield the ion pair $D^+$-$B^-$-A with tau=60 ps, which undergoes a subsequent charge shift with tau=140 ps to yield the long-lived ion pair $D^+$-B-$A^-$ (tau=700 ns). Subsequent selective photoexcitation of B within $D^+$-B-$A^-$ with a 520 nm, 150 fs laser pulse at tau=500 ps results in about 20% of the D+-B-$A^-$ population undergoing charge recombination with tau=100 ps. This charge recombination rate is about 7000 times faster than the normal recombination rate of the ion pair. The results demonstrate that formation of the lowest excited singlet state of the bridge molecule B significantly alters the reaction pathways leading to charge recombination. Thus, D-B-A can be viewed as a molecular switch in which the $D^+$-B-$A^-$ state can be rapidly turned on and off using 400 and 520 nm laser pulses, respectively.

The structural and optical properties of semiconductor block copolymers containing triphenylamine as hole transport material and perylene bisimide as dye and electron transport material was reported (see, Stefan M. Lindner, Nadine Kaufmann, Mukundan Thelakkat, "Nanostructured semiconductor block copolymers: π-π Stacking, optical and electrochemical properties", *Organic Electronics*, 8 (2007), pp. 69-75). The polymers were prepared by nitroxide mediated controlled radical polymerisation and characterized with GPC, DSC, and TGA. The electrochemical properties as determined by cyclic voltammetry show the HOMO and LUMO values of the block copolymers to be −5.23 eV and −3.65 eV, respectively. The perylene bisimide units aggregate by π-π stacking which could be analyzed with wide-angle X-ray scattering. The absorption and fluorescence properties of the perylene bisimide polymers and monomers in solution and film were investigated. It could be shown that they are strongly influenced by intramolecular coupling between different perylene bisimide units in polymers. The block copolymers exhibit a microphase separation on a nano-meter scale with a constant perylene bisimide domain width of 13 nm and lengths of up to several micrometers.

A novel donor acceptor dyad consisting of tetraphenylbenzidine (TPD) and perylene bisimide was synthesized by linking these moieties using a dodecyl spacer (see, Peter Bauer, Helga Wietasch, Stefan M. Lindner, and Mukundan Thelakkat, "Synthesis and Characterization of Donor-Bridge-Acceptor Molecule Containing Tetraphenylbenzidine and Perylene Bisimide", *Chem. Mater.* 2007, 19, 88-94). HOMO and LUMO values of the dyad were acquired by cyclic voltammetry. Photophysical properties were studied by steady-state UV-vis and fluorescence spectroscopy. After selective excitation of the TPD moiety, a quenching of donor fluorescence and the appearance of acceptor fluorescence was observed. This proves nonradiative energy transfer from the donor to the acceptor group. The energy transfer was 4 times more efficient in DBA than in a mixture of D and A. The energy transfer efficiency in the dyad is also independent of the concentration, indicating intramolecular transfer mechanism. However, the direct excitation of the acceptor in the dyad exhibited reduced fluorescence emission of the acceptor, indicating electron transfer between the moieties. Thus, this DBA is an excellent model system for the study of energy- and electron-transfer processes in organic semiconductors.

The general description of the present invention having been made, a further understanding can be obtained by reference to the specific embodiments, which are given herein only for the purpose of illustration and are not intended to limit the scope of the appended claims.

The present invention provides an organic compound and an organic photovoltaic device that overcomes the drawbacks of the prior art organic photovoltaic devices, such as technical difficulties of fabrication and low conversion efficiency of a conventional organic photovoltaic device.

In the first preferred embodiment of the present invention there is provided a predominantly planar organic compound of the general structural formula (I)

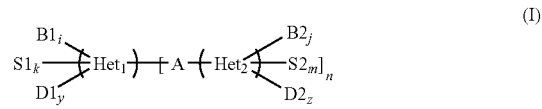

where $Het_1$ is a predominantly planar polycyclic molecular system of first type; $Het_2$ is a predominantly planar polycyclic molecular system of second type; A is a bridging group providing a lateral bond of the molecular system $Het_1$ with the molecular system $Het_2$ via strong chemical bonds; n is 1, 2, 3, 4, 5, 6, 7 or 8; B1 and B2 are binding groups; i is 0, 1, 2, 3, 4, 5, 6, 7 or 8; j is 0, 1, 2, 3, 4, 5, 6, 7 or 8; S1 and S2 are groups providing solubility of the organic compound; k is 0, 1, 2, 3, 4, 5, 6, 7 or 8; m is 0, 1, 2, 3, 4, 5, 6, 7 or 8; D1 and D2 are substituents independently selected from a list comprising —CH$_3$, —C$_2$H$_5$, —C$_3$H$_7$, —NO$_2$, —Cl, —Br, —F, —CF$_3$, —CN, —OH, —OCH$_3$, —OC$_2$H$_5$, —OCOCH$_3$, —OCN, —SCN—NH$_2$, —NHCOCH$_3$, —C$_2$Si(CH$_3$)$_3$, and —CONH$_2$; y is 0, 1, 2, 3, 4, 5, 6, 7 or 8; and z is 0, 1, 2, 3, 4, 5, 6, 7 or 8. Said organic compound absorbs electromagnetic radiation in at least one predetermined spectral subrange within a wavelength range from 400 to 3000 nm and is capable to form supramolecules. The molecular system $Het_1$, the bridging group A, and the molecular system $Het_2$ are capable to form a donor-bridge-acceptor system providing dissociation of excited electron-hole pairs.

In a donor-bridge-acceptor molecule system ($Het_1$-A-$Het_2$, where molecular system $Het_1$ serves as donor, and molecular systems $Het_2$ serve as acceptors) the superexchange mechanism for electron transfer involves mixing of electronic states of the bridging group A with those of the donor and acceptor systems ($Het_1$ and $Het_2$). This mixing depends critically on both the spatial overlap of the molecular orbitals of bridging group A with those of $Het_1$ and $Het_2$ and the vertical energy gap between $^1$*$Het_1$-A-$Het_2$ and the energetically higher lying $Het_1^+$-$A^-$-$Het_2$ state. In principle, several different states of the bridging group A may contribute to the overall electronic coupling between the donor and the acceptor, their relative contributions being determined by the electronic couplings and the energy gaps between the various states.

In one embodiment of the disclosed organic compound, at least one of the polycyclic molecular systems is heterocyclic molecular system. In another embodiment of the present invention a solution of the organic compound or its salt is capable of forming a photovoltaic layer on a substrate. In yet another embodiment of organic compound according to the present invention, the predominantly planar polycyclic molecular system of the first type ($Het_1$) and at least one predominantly planar polycyclic molecular system of the second type ($Het_2$) absorb electromagnetic radiation in different predetermined spectral subranges within a wavelength range from 400 to 3000 nm.

In yet another embodiment, heterocyclic molecular systems may be used as polycyclic molecular systems. In one embodiment of the disclosed organic compound, the strong chemical bond is selected from the list comprising covalent bond, coordination bond, ionic bond, and any combination thereof.

In another embodiment of the disclosed organic compound, said solution is based on water and/or water-miscible solvents and the numbers k and m obey the following condition: $k+m \neq 0$. In still another embodiment of the disclosed organic compound according, at least one of the groups providing a solubility of the organic compound in water and/or water-miscible solvents is independently selected from the list comprising $COO^-$, $SO_3^-$, $HPO_3^-$, and $PO_3^{2-}$ and any combination thereof. In yet another embodiment of the disclosed organic compound, the photovoltaic layer has column-like supramolecules formed by means of π-π-interaction of single-type polycyclic molecular systems and having longitudinal axes oriented predominantly in the substrate plane. In one embodiment of the disclosed organic compound, the column-like supramolecules are positioned predominantly parallel to each other. In another embodiment of the disclosed organic compound, a number and a chain length of the substituents are selected to provide an electric isolation of the adjacent column-like supramolecules.

In one embodiment of the disclosed organic compound, the numbers k and m obey the following condition: $k+m \neq 0$ and said solution is based on organic solvent. In another embodiment of the disclosed organic compound, the organic solvent is selected from the list comprising benzene, toluene, xylenes, acetone, acetic acid, methylethylketone, hydrocarbons, chloroform, carbontetrachloride, methylenechloride, dichlorethane, chlorobenzene, alcohols, nitromethan, acetonitrile, dimethylforamide, 1,4-dioxane, tetrahydrofuran (THF), methylcyclohexane (MCH) or any combination thereof. In still another embodiment of the disclosed organic compound, at least one of the groups providing a solubility of the organic compound in organic solvent is amide of acid residue independently selected from the list comprising $CONR_1R_2$, $CONHCONH_2$, $SO_2NR_1R_2$, and any combination thereof, where $R_1, R_2$ are independently selected from H, alkyl or aryl. In yet another embodiment of the disclosed organic compound, at least one of the groups providing a solubility of the organic compound in organic solvent are independently selected from the list comprising alkyl, aryl, substituted alkyl, substituted aryl and any combination thereof. In one embodiment of the disclosed organic compound, the alkyl group is selected from methyl, ethyl, propyl, butyl, I-butyl and t-butyl groups, and the aryl group is selected from phenyl, benzyl and naphthyl groups. In another embodiment of the organic compound according to present invention, a number and a chain length of the groups providing a solubility of the organic compound in organic solvent are selected to provide an electric isolation of the adjacent stacks. The providing solubility groups create a protective envelope located around of stacks. These envelopes protect molecular systems forming the stack against all interactions except of π-π interaction of the single-type polycyclic molecular systems ($Het_1$ and $Het_2$).

In one embodiment of the disclosed organic compound, the numbers i and j obey the following condition: $i+j \geq 3$; and the photovoltaic layer has planar supramolecules having polycyclic molecular systems with planes oriented predominantly parallel to the substrate plane due to lateral interaction of binding groups by means of strong and weak chemical bonds. In another embodiment of the disclosed organic compound, at least one of said planar supramolecules has the form selected from the list comprising disk, plate, lamella, ribbon or any combination thereof. In still another embodiment of the disclosed organic compound, wherein said weak chemical bond is selected from the list comprising single hydrogen bond, dipole-dipole interaction, cation-π interaction, van der Waals interaction, π-π interaction, and any combination thereof. In yet another embodiment of disclosed organic compound, the planar supramolecules form molecular stacks by means of π-π-interaction of the single-type polycyclic molecular systems providing different current-conducting-paths with electron and hole conductivity respectively. Said molecular stacks are electrically isolated among themselves due to the groups providing solubility of the organic compound.

In one embodiment of the disclosed organic compound, the molecular stacks are oriented predominantly perpendicular to the substrate plane.

In one embodiment of the disclosed organic compound, the predetermined spectral subrange is from 400 to 700 nm. In another embodiment of the disclosed organic compound, at least one of the predominantly planar polycyclic molecular systems is partially or completely conjugated. In still another embodiment of the disclosed organic compound, at least one of the predominantly planar polycyclic molecular systems comprises hetero-atoms selected from the list comprising nitrogen, oxygen, sulfur, and any combination thereof.

In one embodiment of the disclosed organic compound, at least one of the bridging groups is selected from the list comprising imidazole, perylene-3,4-dicarboximide, a series of p-phenylene ($Ph_P$) oligomers, where p is 1, 2, 3, 4 or 5; and a series of 2,7-oligofluorene ($FL_S$) oligomers, where s is 1, 2, 3, or 4.

In one embodiment of the disclosed organic compound, the numbers i and j obey the following condition: $i+j \neq 0$ and at least one of the binding groups is an intra-binding group. In another embodiment of the disclosed organic compound, the intra-binding group is alkyne-comprising group.

In still another embodiment of the disclosed organic compound, the numbers i and j obey the following condition $i+j \neq 0$ and at least one of the binding groups is an inter-binding group. In yet another embodiment of the disclosed organic compound, in which there is at least one intra-binding group the numbers i and j obey the following condition $i+j>1$ and at least one of the binding groups is an inter-binding group. In one embodiment of the disclosed organic compound, at least one of the inter-binding groups is selected from the list comprising the hetero-atoms, COOH, $SO_3H$, $H_2PO_3$, NH, $NH_2$, NHR, $NR_2$, and any combination thereof, where radical R is alkyl or aryl. In another embodiment of the disclosed organic compound, the alkyl group is independently selected from methyl, ethyl, propyl, butyl, I-butyl and t-butyl groups, and the aryl group is selected from phenyl, benzyl and naphthyl groups.

In one embodiment of the disclosed organic compound, at least one of the predominantly planar polycyclic molecular systems $Het_1$ or $Het_2$ comprises phthalocyanine fragments. Table 1 shows some examples of planar polycyclic molecular systems comprising tetrapirolic macro-cyclic fragments of a general structural formula corresponding to structures 1-6, where Latin letter M denotes an atom of metal or two protons (2H).

TABLE 1

Examples of planar polycyclic molecular systems comprising tetrapirolic macrocyclic fragments

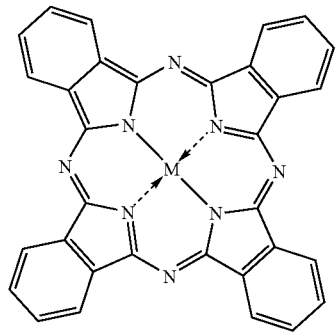

1

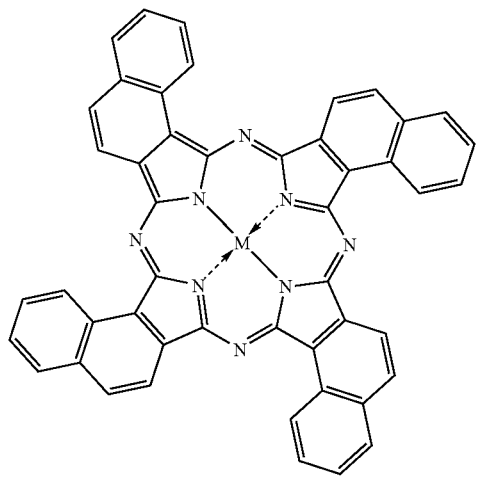

2

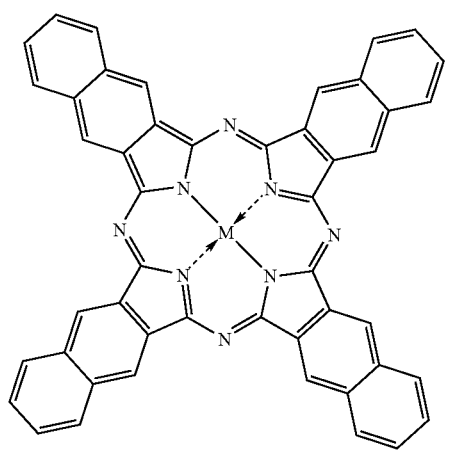

3

TABLE 1-continued

Examples of planar polycyclic molecular systems comprising tetrapirolic macrocyclic fragments

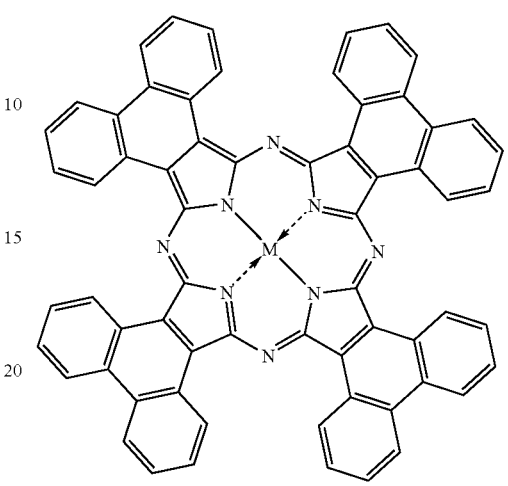

4

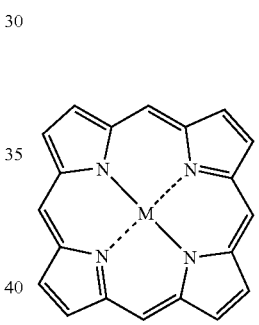

5

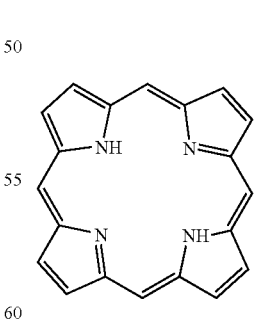

6

In still another embodiment of the disclosed invention, the planar polycyclic molecular system comprises rylene fragments. Table 2 shows some examples of polycyclic molecular systems comprising rylene fragments of a general structural formula corresponding to structures 7-27.

TABLE 2
Examples of polycyclic molecular systems comprising rylene fragments
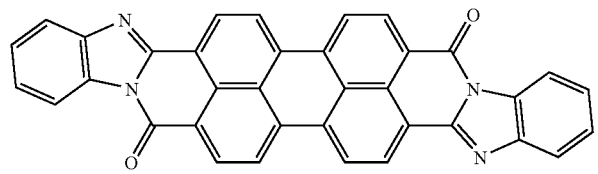 [SMILES: O=c1c2ccc3c4ccc5c6c(ccc(c7ccc(c2c37)c2nc3ccccc3n12)c46)c(=O)n1c2ccccc2nc51]
7
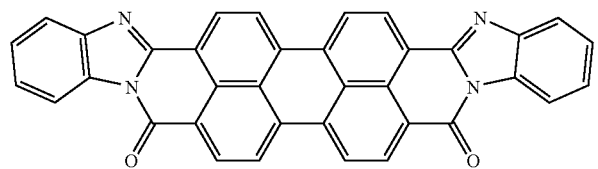 [SMILES: O=c1c2ccc3c4ccc5c(=O)n6c7ccccc7nc6c6ccc(c7ccc(c2c37)c2nc3ccccc3n12)c4c56]
8
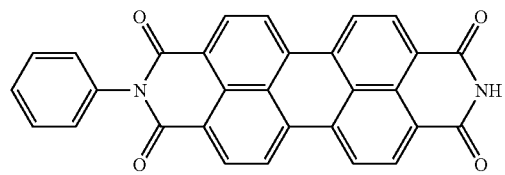 [SMILES: O=C1NC(=O)c2ccc3c4ccc5c6c(ccc(c7ccc1c2c73)c64)C(=O)N(c1ccccc1)C5=O]
9
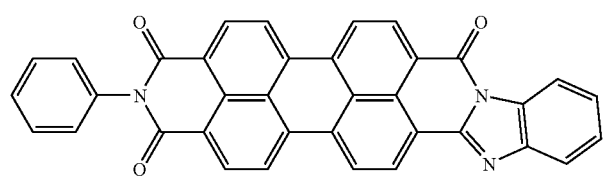 [SMILES: O=C1c2ccc3c4ccc5c(=O)n6c7ccccc7nc6c6ccc(c7ccc(c2c37)C(=O)N1c1ccccc1)c4c56]
10
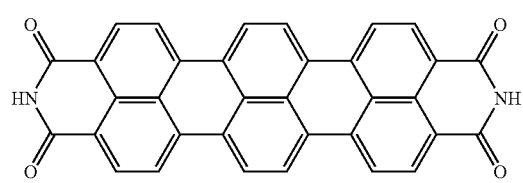
11
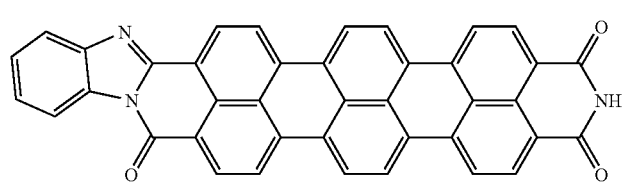 [SMILES: O=C1NC(=O)c2ccc3c4ccc5c6ccc7c8c(ccc(c9ccc(c%10ccc1c2c%103)c4c95)c68)c(=O)n1c2ccccc2nc71]
12
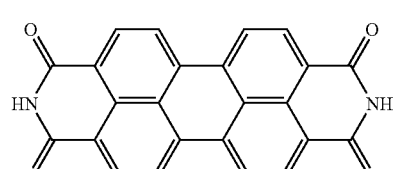
13
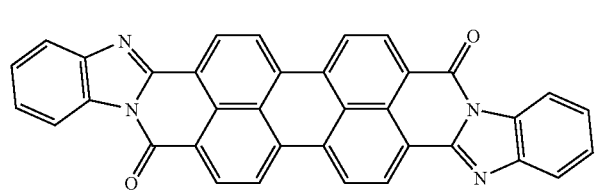 [SMILES: O=c1c2ccc3c4ccc5c6c(ccc(c7ccc(c2c37)c2nc3ccccc3n12)c46)c(=O)n1c2ccccc2nc51]
14

TABLE 2-continued
Examples of polycyclic molecular systems comprising rylene fragments
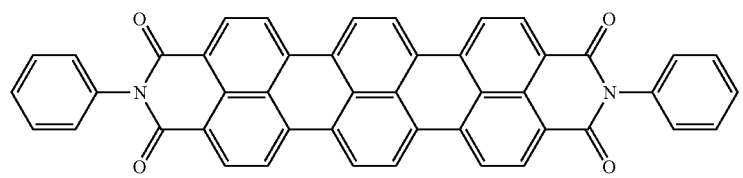 [SMILES: O=C1c2ccc3c4ccc5c6ccc7c8c(ccc(c9ccc(c%10ccc(c2c3%10)C(=O)N1c1ccccc1)c4c59)c86)C(=O)N(c1ccccc1)C7=O]
15
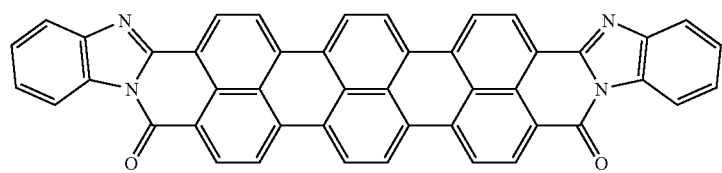 [SMILES: O=c1c2ccc3c4ccc5c6ccc7c(=O)n8c9ccccc9nc8c8ccc(c9ccc(c%10ccc(c2c3%10)c2nc3ccccc3n12)c4c59)c6c78]
16
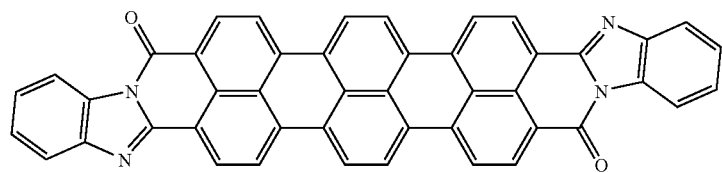 [SMILES: O=c1c2ccc3c4ccc5c6ccc7c8c(ccc(c9ccc(c%10ccc(c2c3%10)c2nc3ccccc3n12)c4c95)c68)c(=O)n1c2ccccc2nc71]
17
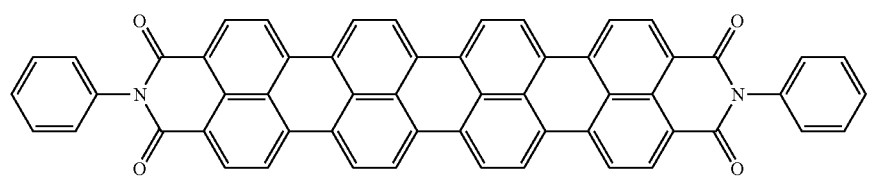 [SMILES: O=C1c2ccc3c4ccc5c6ccc7c8ccc9c%10c(ccc(c%11ccc(c%12ccc(c%13ccc(c2c3%13)C(=O)N1c1ccccc1)c4c5%12)c6c7%11)c%108)C(=O)N(c1ccccc1)C9=O]
18
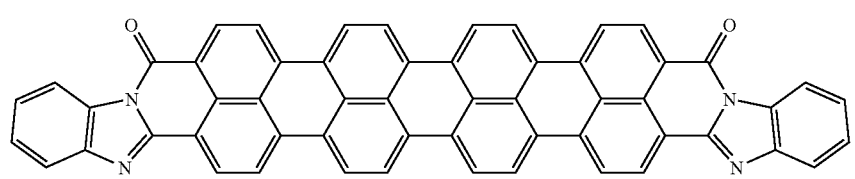 [SMILES: O=c1c2ccc3c4ccc5c6ccc7c8ccc9c(=O)n%10c%11ccccc%11nc%10c%10ccc(c%11ccc(c%12ccc(c%13ccc(c2c3%13)c2nc3ccccc3n12)c4c5%12)c6c7%11)c8c9%10]
19
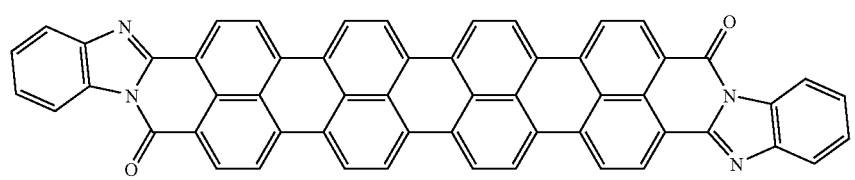 [SMILES: O=c1c2ccc3c4ccc5c6ccc7c8ccc9c%10c(ccc(c%11ccc(c%12ccc(c%13ccc(c2c3%13)c2nc3ccccc3n12)c4c5%12)c6c%117)c8%10)c(=O)n1c2ccccc2nc91]
20
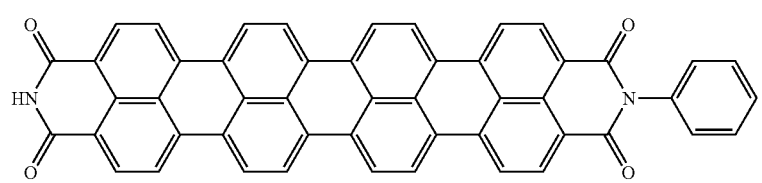 [SMILES: O=C1NC(=O)c2ccc3c4ccc5c6ccc7c8ccc9c%10c(ccc(c%11ccc(c%12ccc(c%13ccc1c2c%133)c4c%125)c6c%117)c%108)C(=O)N(c1ccccc1)C9=O]
21
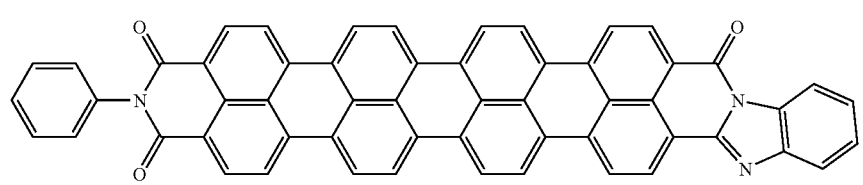 [SMILES: O=C1c2ccc3c4ccc5c6ccc7c8ccc9c(=O)n%10c%11ccccc%11nc%10c%10ccc(c%11ccc(c%12ccc(c%13ccc(c2c3%13)C(=O)N1c1ccccc1)c4c5%12)c6c7%11)c8c9%10]
22

TABLE 2-continued

Examples of polycyclic molecular systems comprising rylene fragments

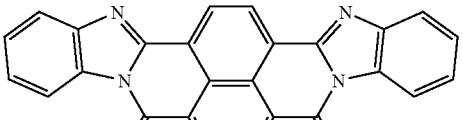

In another embodiment of the disclosed invention, the planar polycyclic molecular system may comprise naphthalene fragments. Table 3 shows some examples of planar polycyclic molecular systems comprising such naphthalene fragments of a general structural formula corresponding to structures 28-29.

TABLE 3

Examples of planar polycyclic molecular systems comprising naphthalene fragments

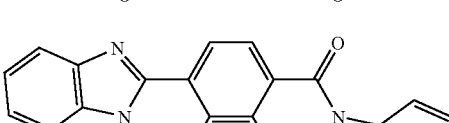

In the second preferred embodiment of the present invention there is provided an organic photovoltaic layer that comprises at least one organic compound having the general structural formula II:

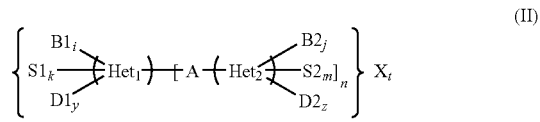

where $Het_1$ is a predominantly planar polycyclic molecular system of first type; $Het_2$ is a predominantly planar polycyclic molecular system of second type; A is a bridging group providing a lateral bond of the molecular system $Het_1$ with the molecular system $Het_2$ via strong chemical bonds; n is 1, 2, 3, 4, 5, 6, 7 or 8; B1 and B2 are binding groups; i is 0, 1, 2, 3, 4, 5, 6, 7 or 8; j is 0, 1, 2, 3, 4, 5, 6, 7 or 8; S1 and S2 are groups providing solubility of the organic compound; k is 0, 1, 2, 3, 4, 5, 6, 7 or 8; m is 0, 1, 2, 3, 4, 5, 6, 7 or 8; D1 and D2 are substituents independently selected from a list comprising —$CH_3$, —$C_2H_5$, —$C_3H_7$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$; and y is 0, 1, 2, 3, 4, 5, 6, 7 or 8; z is 0, 1, 2, 3, 4, 5, 6, 7 or 8; X is a counterion from a list comprising $H^+$, $Li^+$, $Na^+$, $K^+$, $NH_4^+$, $Ba^{++}$, $Zn^{++}$, $Sr^{++}$, $Ca^{++}$, $Mg^{++}$, and any combination thereof; t is the number of counterions providing for the electric neutrality of the organic compound. The photovoltaic layer has absorption of electromagnetic radiation in at least one predetermined spectral subrange within a wavelength range from 400 to 3000 nm and is capable to form supramolecules. The molecular system $Het_1$, the bridging group A, and the molecular system $Het_2$ are capable to form donor-bridge-acceptor system providing dissociation of excited electron-hole pairs.

In one embodiment of the disclosed organic photovoltaic layer, at least one of the polycyclic molecular systems is heterocyclic molecular system. In another embodiment of the disclosed organic photovoltaic layer, the predominantly planar polycyclic molecular system of first type ($Het_1$) and at least one predominantly planar polycyclic molecular system of second type ($Het_2$) absorb electromagnetic radiation in different predetermined spectral subranges within a wavelength range from 400 to 3000 nm.

In one embodiment of the disclosed organic photovoltaic layer, the strong chemical bond is selected from the list comprising covalent bond, coordination bond, ionic bond, and any combination thereof.

In another embodiment of the disclosed organic photovoltaic layer, the photovoltaic layer has column-like supramolecules formed by means of π-π-interaction of single-type polycyclic molecular systems and having longitudinal axes oriented predominantly in the layer plane. In still another embodiment of the disclosed organic photovoltaic layer, the column-like supramolecules are positioned predominantly parallel to each other. In one embodiment of the organic photovoltaic layer according to present invention, a number and a chain length of the substituents are selected to provide an electric isolation of the adjacent column-like supramolecules. In another embodiment of disclosed organic photovoltaic layer, the photovoltaic layer comprises photovoltaic fibers oriented predominantly parallel to each other in the layer plane.

In still another embodiment of the organic photovoltaic layer according to present invention, the photovoltaic layer comprises at least one woven photovoltaic layer comprising photovoltaic fibers, wherein the photovoltaic fibers are arranged predominantly parallel to each other.

In yet another embodiment of the disclosed organic photovoltaic layer, the photovoltaic layer has planar supramolecules having polycyclic molecular systems with planes oriented predominantly parallel to the layer plane due to lateral interaction of binding groups by means of strong and weak chemical bonds. In one embodiment of the disclosed organic photovoltaic layer, at least one of said planar supramolecules has the form selected from the list comprising disk, plate, lamella, ribbon or any combination thereof. In another embodiment of the disclosed organic photovoltaic layer, the weak chemical bond is selected from the list comprising single hydrogen bond, dipole-dipole interaction, cation-π interaction, van der Waals interaction, π-π interaction, and any combination thereof. In still another embodiment of the disclosed organic photovoltaic layer, the planar supramolecules form molecular stacks by means of π-π-interaction of the single-type polycyclic molecular systems providing different current-conducting-paths with electron and hole conductivity respectively, wherein said molecular stacks are electrically isolated among themselves due to the substituents or/and groups providing solubility of the organic compound. In yet another embodiment of the disclosed organic photovoltaic layer, the molecular stacks are oriented predominantly perpendicular to the plane of the photovoltaic layer.

In one embodiment of the disclosed organic photovoltaic layer, the predetermined spectral subrange is from 400 to 700 nm. In another embodiment of the disclosed organic photovoltaic layer, at least one of the predominantly planar polycyclic molecular systems is partially or completely conjugated. In still another embodiment of the disclosed organic photovoltaic layer, at least one of the predominantly planar polycyclic molecular systems comprises the hetero-atoms selected from the list comprising nitrogen, oxygen, sulfur, and any combination thereof.

In one embodiment of the disclosed organic photovoltaic layer, at least one of the bridging groups is selected from the list comprising an imidazole, perylene-3,4-dicarboximide, a series of p-phenylene ($Ph_P$) oligomers, where p is 1, 2, 3, 4 or 5; and a series of 2,7-oligofluorene ($FL_S$) oligomers, where s is 1, 2, 3, or 4.

The examples of polycyclic molecular systems of a general structural formula corresponding to structures 1-29 shown in Tables 1-3 serve to illustrate the invention without limiting it. In one embodiment of the disclosed organic photovoltaic layer, the planar polycyclic molecular system comprises tetrapirolic macro-cyclic fragments. Some examples of such planar polycyclic molecular systems comprising tetrapirolic macro-cyclic fragments having a general structural formula from the group comprising structures 1-6 are given in Table 1 where Latin letter M denotes an atom of metal or two protons (2H). In another embodiment of the disclosed organic photovoltaic device, the planar polycyclic molecular system comprises rylene fragments. Some examples of such planar polycyclic molecular systems comprising rylene fragments having a general structural formula from the group comprising structures 7-27 are given in Table 2. In another embodiment of the disclosed organic photovoltaic layer, the planar polycyclic molecular system comprises naphthalene fragments. Some examples of such polycyclic molecular systems having a general structural formula from the group comprising structures 28-29 are given in Table 3.

In one embodiment of the disclosed organic photovoltaic layer, the molecular stacks are oriented predominantly perpendicular to the plane of the photovoltaic layer. In one embodiment of the disclosed organic photovoltaic layer, the parallel column-like supramolecules are oriented predominantly in the plane of the photovoltaic layer.

In yet another embodiment of the present invention, the photovoltaic layer comprises the parallel photovoltaic fibers oriented predominantly in the plane of the photovoltaic layer.

In a third preferred embodiment of the present invention there is provided an organic photovoltaic device comprising the first and second electrodes and at least one photovoltaic layer having the front surface and the rear surface, wherein said photovoltaic layer comprises at least one organic compound having the general structural formula II:

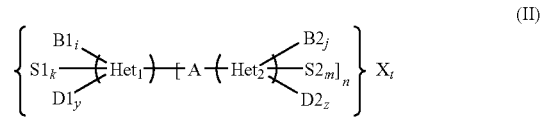

(II)

where $Het_1$ is a predominantly planar polycyclic molecular system of first type; $Het_2$ is a predominantly planar polycyclic molecular system of second type; A is a bridging group providing a lateral bond of the molecular system $Het_1$ with the molecular system $Het_2$ via strong chemical bonds; n is 1, 2, 3, 4, 5, 6, 7 or 8; B1 and B2 are binding groups; i is 0, 1, 2, 3, 4, 5, 6, 7 or 8; j is 0, 1, 2, 3, 4, 5, 6, 7 or 8; S1 and S2 are groups providing solubility of the organic compound; k is 0, 1, 2, 3, 4, 5, 6, 7 or 8; m is 0, 1, 2, 3, 4, 5, 6, 7 or 8; D1 and D2 are substituents independently selected from a list comprising —$CH_3$, —$C_2H_5$, —$C_3H_7$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$; and y is 0, 1, 2, 3, 4, 5, 6, 7 or 8; z is 0, 1, 2, 3, 4, 5, 6, 7 or 8; X is a counterion from a list comprising $H^+$, $Li^+$, $Na^+$, $K^+$, $NH_4^+$, $Ba^{++}$, $Zn^{++}$, $Sr^{++}$, $Ca^{++}$, $Mg^{++}$, and any combination thereof; t is the number of counterions providing for the electric neutrality of the organic compound. The photovoltaic layer has absorption of electromagnetic radiation in at least one predetermined spectral subrange within a wavelength range from 400 to 3000 nm and is capable to form supramolecules. The molecular system $Het_1$, the bridging group A, and the molecular system $Het_2$ are capable to form donor-bridge-acceptor system providing dissociation of excited electron-hole pairs.

In one embodiment of the disclosed organic photovoltaic device, at least one of the polycyclic molecular systems is heterocyclic molecular system. In another embodiment of the disclosed organic photovoltaic device, the predominantly planar polycyclic molecular system of first type ($Het_1$) and at least one predominantly planar polycyclic molecular system of second type ($Het_2$) absorb electromagnetic radiation in different predetermined spectral subranges within a wavelength range from 400 to 3000 nm.

Disclosed organic photovoltaic device possesses a number of advantages in comparison with usual devices on the basis of organic compounds and inorganic materials. The donor-bridge-acceptor systems provide dissociation of excited electron-hole pairs and mobile carriers (electrons and holes) go along different current-conducting paths practically simultaneously with absorption of quantum of electromagnetic radiation. The choice of molecular system of the first type $Het_1$ and various molecular systems of the second type $Het_2$ allows adjusting (expanding or narrowing) of an absorption band and to optimize transformation efficiency of the disclosed organic photovoltaic device. The donor-bridge-acceptor systems can comprise both donor and acceptor absorbing molecular systems ($Het_1$, and $Het_2$).

In one embodiment of the disclosed organic photovoltaic device, the strong chemical bond is selected from the list comprising covalent bond, coordination bond, ionic bond, and any combination thereof.

In another embodiment of the disclosed organic photovoltaic device, the photovoltaic layer has column-like supramolecules formed by means of π-π-interaction of single-type polycyclic molecular systems and having longitudinal axes oriented predominantly in the layer plane. In still another embodiment of the disclosed organic photovoltaic device, the column-like supramolecules are positioned predominantly parallel to each other. In one embodiment of the organic photovoltaic device according to present invention, a number and a chain length of the substituents are selected to provide an electric isolation of the adjacent column-like supramolecules. In another embodiment of disclosed organic photovoltaic device, the photovoltaic layer comprises photovoltaic fibers oriented predominantly parallel to each other in the layer plane. In still another embodiment of the organic photovoltaic device according to present invention comprises at least one woven photovoltaic layer comprising photovoltaic fibers, wherein the photovoltaic fibers are arranged predominantly parallel to each other.

In yet another embodiment of the disclosed organic photovoltaic device, the photovoltaic layer has planar supramolecules having polycyclic molecular systems with planes oriented predominantly parallel to the layer plane due to lateral interaction of binding groups by means of strong and weak chemical bonds. In one embodiment of the disclosed organic photovoltaic device, at least one of said planar supramolecules has the form selected from the list comprising disk, plate, lamella, ribbon or any combination thereof. In another embodiment of the disclosed organic photovoltaic device, the weak chemical bond is selected from the list comprising single hydrogen bond, dipole-dipole interaction, cation-π interaction, van der Waals interaction, π-π interaction, and any combination thereof. In still another embodiment of the disclosed organic photovoltaic device, the planar supramolecules form molecular stacks by means of π-π-interaction of the single-type polycyclic molecular systems providing different current-conducting-paths with electron and hole conductivity respectively, wherein said molecular stacks are electrically isolated among themselves due to the substituents or/and groups providing solubility of the organic compound. In yet another embodiment of the disclosed organic photovoltaic device, the molecular stacks are oriented predominantly perpendicular to the plane of the photovoltaic layer.

In one embodiment of the disclosed organic photovoltaic device, the predetermined spectral subrange is from 400 to 700 nm. In another embodiment of the disclosed organic photovoltaic device, at least one of the predominantly planar polycyclic molecular systems is partially or completely conjugated. In still another embodiment of the disclosed organic photovoltaic device, at least one of the predominantly planar polycyclic molecular systems comprises the hetero-atoms selected from the list comprising nitrogen, oxygen, sulfur, and any combination thereof.

In one embodiment of the disclosed organic photovoltaic device, at least one of the bridging groups is selected from the list comprising an imidazole, perylene-3,4-dicarboximide, a series of p-phenylene ($Ph_P$) oligomers, where p is 1, 2, 3, 4 or 5; and a series of 2,7-oligofluorene ($FL_S$) oligomers, where s is 1, 2, 3, or 4.

The examples of polycyclic molecular systems of a general structural formula corresponding to structures 1-28 shown in Tables 1-3 serve to illustrate the invention without limiting it. In one embodiment of the disclosed organic photovoltaic device, the planar polycyclic molecular system comprises tetrapirolic macro-cyclic fragments. Some examples of such planar polycyclic molecular systems comprising tetrapirolic macro-cyclic fragments having a general structural formula from the group comprising structures 1-5 are given in Table 1 where Latin letter M denotes an atom of metal or two protons (2H). In another embodiment of the disclosed organic photovoltaic device, the planar polycyclic molecular system comprises rylene fragments. Some examples of such planar polycyclic molecular systems comprising rylene fragments having a general structural formula from the group comprising structures 6-26 are given in Table 2. In another embodiment of the disclosed organic photovoltaic device, the planar polycyclic molecular system comprises naphthalene fragments. Some examples of such polycyclic molecular systems having a general structural formula from the group comprising structures 27-28 are given in Table 3.

In one embodiment of the disclosed organic photovoltaic device, at least one of said electrodes is transparent for the incident electromagnetic radiation to which said organic photovoltaic device is sensitive. In another embodiment of the disclosed organic photovoltaic device, contains one said photovoltaic layer, having the molecular stacks oriented predominantly perpendicular to the plane of the photovoltaic layer, the first electrode formed at least on a part of the front surface of said photovoltaic layer and the second electrode formed at least on a part of the rear surface of said photovoltaic layer. In one embodiment of the disclosed organic photovoltaic device, the second electrode is a reflective electrode for electromagnetic radiation incident upon the device. In one embodiment of the present invention, the disclosed organic photovoltaic device comprises at least one photovoltaic layer having the parallel column-like supramolecules oriented predominantly in the plane of the photovoltaic layer, the first electrode formed in grooves made on a part of one of the surfaces of said photovoltaic layer and the second electrode formed in other grooves made on another part of the same surface of said photovoltaic layer. In yet another embodiment of the present invention, the disclosed organic photovoltaic device comprises at least one photovoltaic layer having the parallel photovoltaic fibers oriented predominantly in the plane of the photovoltaic layer, the first electrode formed in grooves made on a part of one of the surfaces of said photovoltaic layer and the second electrode formed in other grooves made on another part of the same surface of said photovoltaic layer. In still another embodiment of the disclosed organic photovoltaic device, the second electrode is a reflective electrode for the electromagnetic radiation incident upon the device, and the device further comprises an additional retarder layer which is located between said reflective electrode and said photoelectric layer, wherein the thickness and optical anisotropy of said retarder layer are selected so as to ensure a 45° rotation of the polarization vector of said electromagnetic radiation. In one embodiment of the disclosed organic photovoltaic device, the first and second electrodes are finger-like electrodes and form an interdigitated structure and the column-like supramolecules are oriented perpendicularly to a direction of electrodes. In another embodiment of the disclosed organic photovoltaic device, a cross-section of at least one finger-like electrode has the form selected from the list comprising triangle, rectangle, square, circle, V-shaped form, and any combination thereof. In yet another embodiment of the disclosed organic photovoltaic device, the first electrode is made of material with work function providing a hole-harvesting contact and a barrier contact for electrons and the second electrode is made of material with work function providing a barrier contact for holes and an electron-harvesting contact. In still another embodiment of the disclosed organic photovoltaic device, the first electrode comprises an electron-acceptor layer contacting with photovoltaic layer and the second electrode comprises an electron-donor layer contacting with photovoltaic layer. In yet another embodiment of the disclosed organic photovoltaic device, the first electrode is made of material with work function providing a hole-harvesting contact and a barrier contact for electrons and the second electrode is made of material with work function providing a barrier contact for holes and an electron-harvesting contact. In one embodiment the material of the electrode is selected from the list comprising aluminum, ITO (indium tin oxide), carbon nanotube conductive coatings, PEDOT, PEDOT:PSS layers, LiF, and aluminum-doped zinc oxide.

In one embodiment of the disclosed invention, the organic photovoltaic device further comprises a substrate bearing said electrodes and said photovoltaic layer. In another embodiment of the disclosed organic photovoltaic device, the substrate is made of a polymer. In still another embodiment of the disclosed organic photovoltaic device, the substrate is made of a glass. In one embodiment of the disclosed organic photovoltaic device, the substrate is transparent for the incident electromagnetic radiation to which the given optoelectronic device is sensitive.

In yet another embodiment of the disclosed invention, the organic photovoltaic device comprises two or more photovoltaic layers, wherein said layers contain different organic compounds having the general structural formula II, ensuring the absorption of electromagnetic radiation in different spectral subranges within a wavelength range from 400 to 3000 nm.

A more complete assessment of the present invention and its advantages will be readily achieved as the same becomes better understood by reference to the following detailed description, considered in connection with the accompanying drawings and detailed specification, all of which forms a part of the disclosure. Embodiments of the invention are illustrated, by way of example only, in the following Figures, of which:

BRIEF DESCRIPTION OF THE DRAWINGS

FIG. 1 presents a schematic diagram of the disclosed organic compound based on one predominantly planar polycyclic molecular system of first type $Het_1$ and four predominantly planar polycyclic molecular systems of second type $Het_2$. The bridging groups A provide lateral bonds of the molecular system $Het_1$ with the molecular systems $Het_2$ via strong chemical bonds and form donor-bridge-acceptor systems. The molecular system $Het_1$ comprises two binding groups (B1), one group providing solubility of the organic compound (S1) and one substituent (D1). The molecular systems $Het_2$ comprise one binding group (B2), one group providing solubility of the organic compound (S2) and one substituent (D2).

FIG. 2 schematically shows column-like supramolecules formed by means of π-π-interaction of single-type polycyclic molecular systems $Het_1$ and $Het_2$ shown in FIG. 1 (for simplicity the groups of A, B, S and D type are not shown in FIG. 2). In one embodiment the molecular system $Het_1$ is donor of electrons and molecular system $Het_2$ is acceptor of electrons. In this embodiment the molecular systems $Het_1$ form molecular stack providing hole transport path and the molecular systems $Het_2$ form four molecular stacks providing electron transport paths. In another embodiment of organic compound, the column-like supramolecules may comprise intra-binding groups. In this case said intra-binding groups reduce vibrating fluctuations of polycyclic molecular systems that lead to increasing of rigidity and therefore electrical conductivity of molecular stacks. In still another embodiment of organic compound, the column-like supramolecules may comprise inter-binding groups. In this case said inter-binding groups can connect the adjacent supramolecules forming three dimension networks.

FIG. 3 schematically shows another embodiment of an organic compound according present invention, wherein n=1, i=3, k=0, y=0, j=1, m=0 and z=0. In one embodiment of organic compound, the bridging group A provides a lateral bond of the molecular system $Het_1$ with the molecular system $Het_2$ via covalent chemical bonds. In another embodiment of organic compound, the bridging group A provides a lateral bond of the molecular system $Het_1$ with the molecular system $Het_2$ via coordination chemical bonds.

FIG. 4 schematically shows a fragment of disk-like planar supramolecule made of the organic compound shown in FIG. 3 and formed due to lateral interaction of binding groups by means of strong and weak chemical bonds. In one embodiment these disk-like planar supramolecules may be arranged one above another. In this embodiment the single-type polycyclic molecular systems of the adjacent planar supramolecules form molecular stacks by means of π-π-interaction.

FIG. 5 schematically shows a fragment of ribbon-like planar supramolecule. In one embodiment of organic compound, the bridging group A provides a lateral bond of the molecular system $Het_1$ with the molecular system $Het_2$ via covalent chemical bonds. In another embodiment of organic compound, the bridging group A provides a lateral bond of the molecular system $Het_1$ with the molecular system $Het_2$ via coordination chemical bonds. In this embodiment of invention, the binding groups B1 provides a lateral bond of the molecular systems $Het_1$ with each other via strong chemical bonds. In turn, the binding groups B2 provides a lateral bond of the molecular systems $Het_2$ with each other via strong chemical bonds too. The strong chemical bonds create chains —B1-$Het_1$-B1-B1-$Het_1$-B1-B1-$Het_1$-B1- and —B2-$Het_2$-B2-B2-$Het_2$-B2-B2-$Het_2$-B2- with high electrical conductivity.

Figures from 6 to 10 show several embodiments of an organic compound according to present invention. FIG. 6 shows a Tetrakis(N-Alkyl-5,12-bis(trimethylsilylethynyl)-anthra[2,1,9-def:6,5,10-d'e'f']diisoquinoline-1,3,8,10-tetrone-N-phenylen-4-yl) porphyrin, FIG. 7 shows a Tetrakis(N-Alkyl-5,12-bis(trimethylsilylethynyl)-anthra[2,1,9-def:6,5,10-d'e'f']diisoquinoline-1,3,8,10-tetrone-N-biphenylen-4-ylimide) of octacarboxyphthalocyanine, FIG. 8 shows a Tetrakis(BenzoimidazoPeryleneTetraCarboxImid-p-PhenylenePyrrol-dion) Copper Phthalocyanine (TBIPTCI-p-PP-CuPc), FIG. 9 shows a Tetrakis(DiPhenylImidePeryleneTetraCarboxylicAcid) Copper Phthalocyanine (TDPIPTCA-CuPc), and FIG. 10 shows a 2,9-Bis(tris(N,N',N"-alkyl)-octacarboxyphthalocyanine-N'''-4-phenylenyl)-5,12-bis(trimethylsilylethynyl)-anthra[2,1,9-def:6,5,10-d'e'f']diisoquinoline-1,3,8,10-tetrone.

FIG. 11 schematically shows the cross section of an organic photovoltaic device according to present invention. In one embodiment of an organic photovoltaic device, the photovoltaic layer is located between two electrodes (3) and (4). Said photovoltaic layer is formed by an organic compound, comprising the predominantly planar polycyclic molecular system $Het_1$ with p-type conductivity and the predominantly planar polycyclic molecular systems $Het_2$ with n-type conductivity. The organic compound comprises bridging groups. The bridging groups provide a lateral bond of the molecular system $Het_1$ with the molecular system $Het_2$ via strong chemical bonds. The organic compound absorbs electromagnetic radiation in at least one predetermined spectral subrange within a wavelength range from 400 to 3000 nm and is capable to form planar supramolecules. The molecular system $Het_1$, the bridging groups, and the molecular system $Het_2$ are capable to form a donor-bridge-acceptor system providing dissociation of excited electron-hole pairs. The planar supramolecules have polycyclic molecular systems with planes oriented predominantly parallel to the planes of electrodes due to lateral interaction of binding groups by means of strong and weak chemical bonds. The single-type polycyclic molecular systems of the adjacent planar supramolecules form molecular stacks (1) and (2) by means of π-π-interaction. In one embodiment the molecular stacks (1) are conductors of electrons (marked by white arrows) and the molecular stacks (2) are conductors of holes (marked by black arrows). Under action of light hν a photocurrent is formed in the organic photovoltaic device. This photocurrent flows through resistive load (5).

FIG. 12 is an energy band diagram of non-irradiated donor-bridge-acceptor system in equilibrium state formed by said p- and n-type molecular stacks connected by the bridging groups. In this Figure the following designations are used: AEp, IPp and EGp are electron affinity, ionization potential and gap energy of the p-type polycyclic molecular system and AEn, IPn and EGn are electron affinity, ionization potential and gap energy of the n-type polycyclic molecular system. Fermi's level (F-level) is identical to the molecular systems of p- and n-type.

FIG. 13 is an energy band diagram of irradiated donor-bridge-acceptor system formed by p- and n-type molecular stacks connected by bridging groups. The Voc is open-circuit voltage; Vbi is built-in potential; $\phi_N$ is potential barrier for electrons; $\phi_P$ is potential barrier for holes. The excited electron-hole pairs (excitons) are dissociated on border between molecular systems. The FIG. 13 shows that an electron excited in the molecular system of p-type is passed into the molecular system of n-type and hole excited in the molecular system of p-type is reflected from potential barrier $\phi_P$. For effective exciton dissociation it is necessary that the potential barrier $\phi_P$ obeys the following condition: $\phi_P > 3$ kT, where k is the Boltzmann constant, T is the absolute temperature in K. On the other hand, an electron excited in the molecular system of n-type is reflected from potential barrier $\phi_N$ and hole excited in the molecular system of n-type is passed into the molecular system of p-type. It is necessary that the potential barrier $\phi_N$ obeys the following condition: $\phi_N > 3$ kT. The electrode (4) (shown in FIG. 11) provides a hole-harvesting contact with energy band diagram shown in FIG. 14 and barrier contact for electrons with energy band diagram shown in FIG. 15. On the other hand, the electrode (3) (shown in FIG. 11) provides an electron-harvesting contact with energy band diagram shown in FIG. 16 and barrier contact for holes with energy band diagram shown in FIG. 17.

FIG. 18 presents a schematic diagram of the disclosed organic photovoltaic device, based on photovoltaic layer (6) located between the front electrode (3) and the rear electrode (4). At least one of said electrodes is transparent for the incident electromagnetic radiation to which said photovoltaic organic layer is sensitive. The front electrode shown in FIG. 18 is transparent. Said photovoltaic layer (6) comprises the molecular stacks oriented predominantly perpendicular to the plane of the photovoltaic layer. The molecular stacks of planar supramolecules are formed by means of π-π-interaction of the single-type polycyclic molecular systems providing different current-conducting-paths with electron and hole conductivity respectively. These current-conducting-paths are electrically isolated among themselves due to the groups providing solubility of the organic compound. The entire structure is formed on a substrate (7) and the electrodes are connected to a resistive load (5).

FIG. 19 schematically shows a top view of the molecular stack formed by planar supramolecules comprising predominantly planar polycyclic molecular systems (Het$_1$ and Het$_2$) connected by bridging groups (A). In one embodiment, the polycyclic molecular systems (Het$_1$) form current-conducting-path with electron conductivity, the other polycyclic molecular systems (Het$_2$) form current-conducting-path with hole conductivity. These current-conducting-paths are surrounded with the groups providing solubility of the organic compound (S1 and S2). These groups electrically isolate adjacent molecular stacks from each other.

FIG. 20 schematically shows the disclosed organic photovoltaic device, based on photovoltaic layer (6) located between the front electrode (3) made of aluminum and the rear electrode (4) made of ITO. The photovoltaic layer (6) comprises the molecular stacks oriented predominantly perpendicular to the plane of the photovoltaic layer. The disclosed organic photovoltaic device further comprises resistive load (5), an electron acceptor layer (8) and electron donor layer (9).

FIG. 21 schematically shows another embodiment of organic photovoltaic device according present invention. The photovoltaic layer (6) is located between the electron acceptor layer (8) and the electron donor layer (9). The photovoltaic layer (6) comprises the molecular stacks oriented predominantly perpendicular to the plane of the photovoltaic layer. The front electrode (3) is transparent and made of aluminum. The reflective electrode (10) is required to provide that the incident radiation would be doubly transmitted through the photovoltaic layer (6), thus increasing the conversion efficiency of the organic photovoltaic device. The disclosed photovoltaic device further comprises resistive load (5) and substrate (7).

Figure 1:
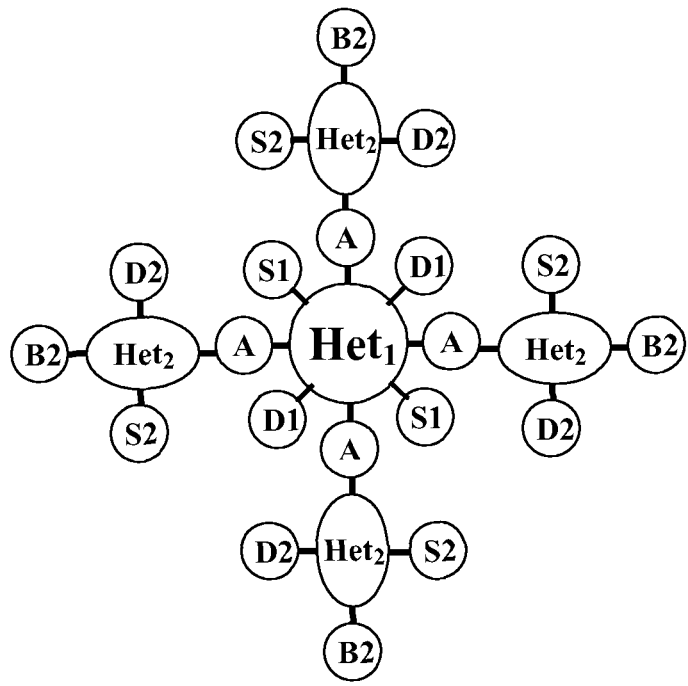
FIG. 1 schematically shows one embodiment of an organic compound according present invention, wherein n=4, i=2, k=1, y=1, j=1, m=1 and z=1.
Figure 2:
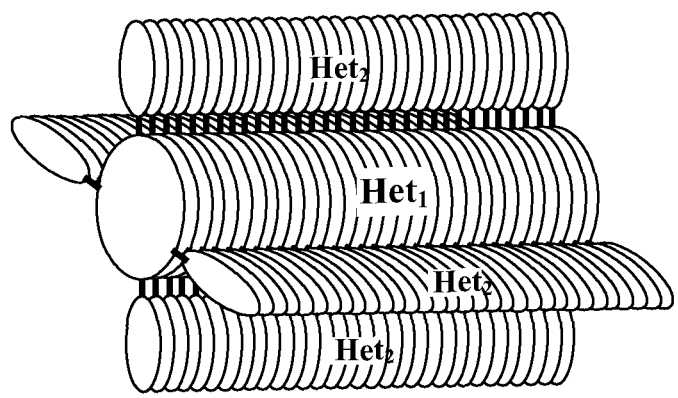
FIG. 2 schematically shows column-like supramolecules formed by means of π-π-interaction of single-type polycyclic molecular systems $Het_1$ and $Het_2$ shown in FIG. 1 (for simplicity the groups of A, B, S and D type are not shown in FIG. 2).
Figure 3:
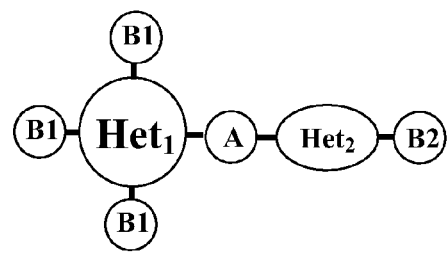
FIG. 3 schematically shows another embodiment of an organic compound according present invention, wherein n=1, i=3, k=0, y=0, j=1, m=0 and z=0.
Figure 4:
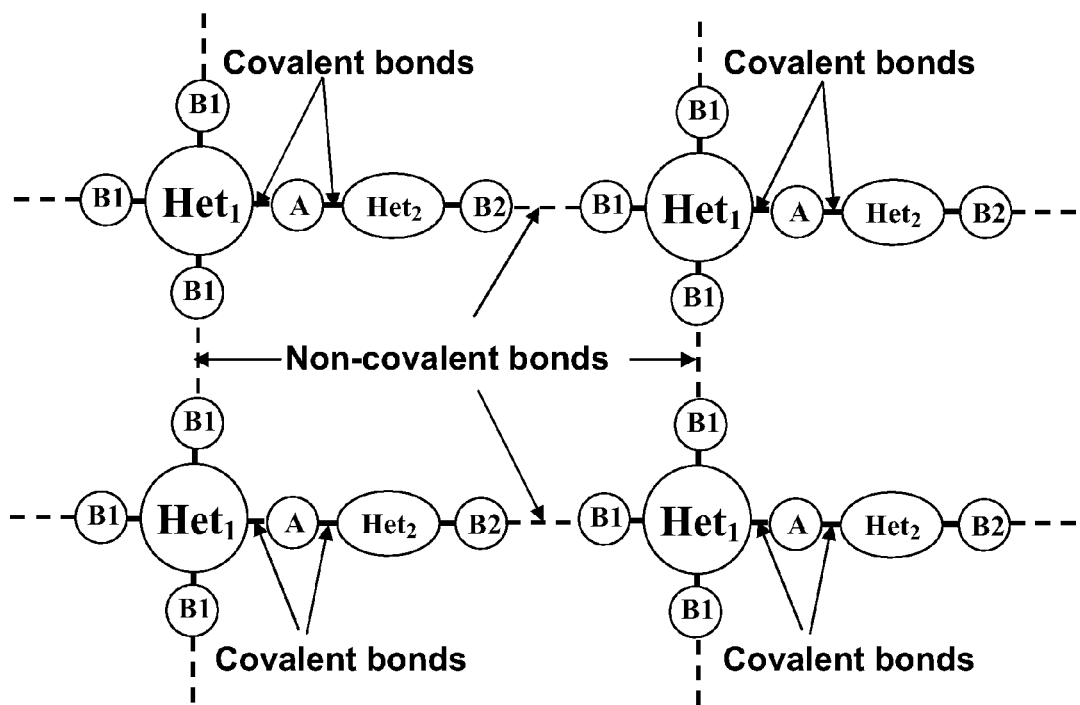
FIG. 4 schematically shows a fragment of disk-like planar supramolecule made of the organic compound shown in FIG. 3 and formed by means of strong and weak chemical bonds.
Figure 5:
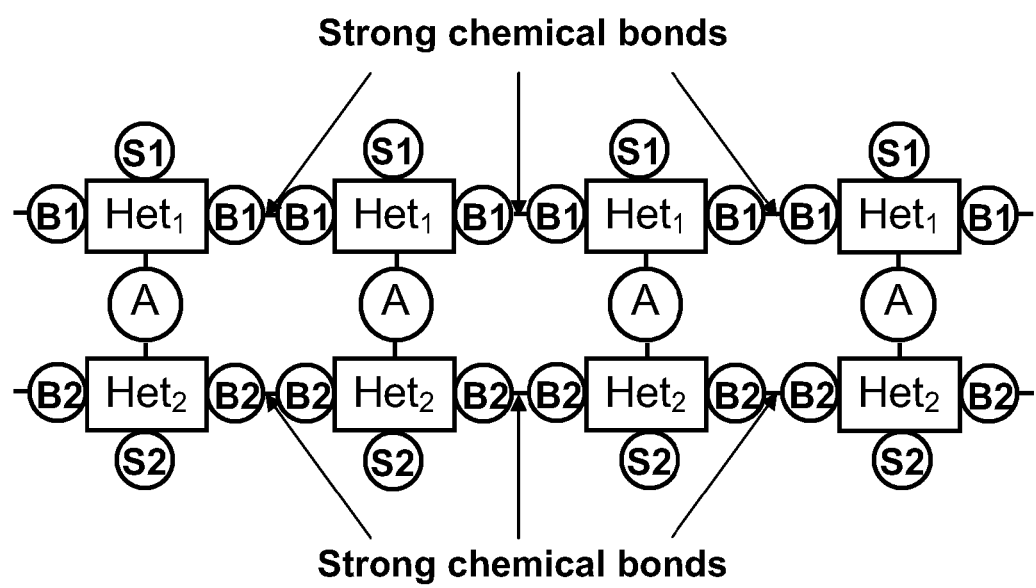
FIG. 5 schematically shows a fragment of ribbon-like planar supramolecule formed by means of strong chemical bonds.
Figure 6:
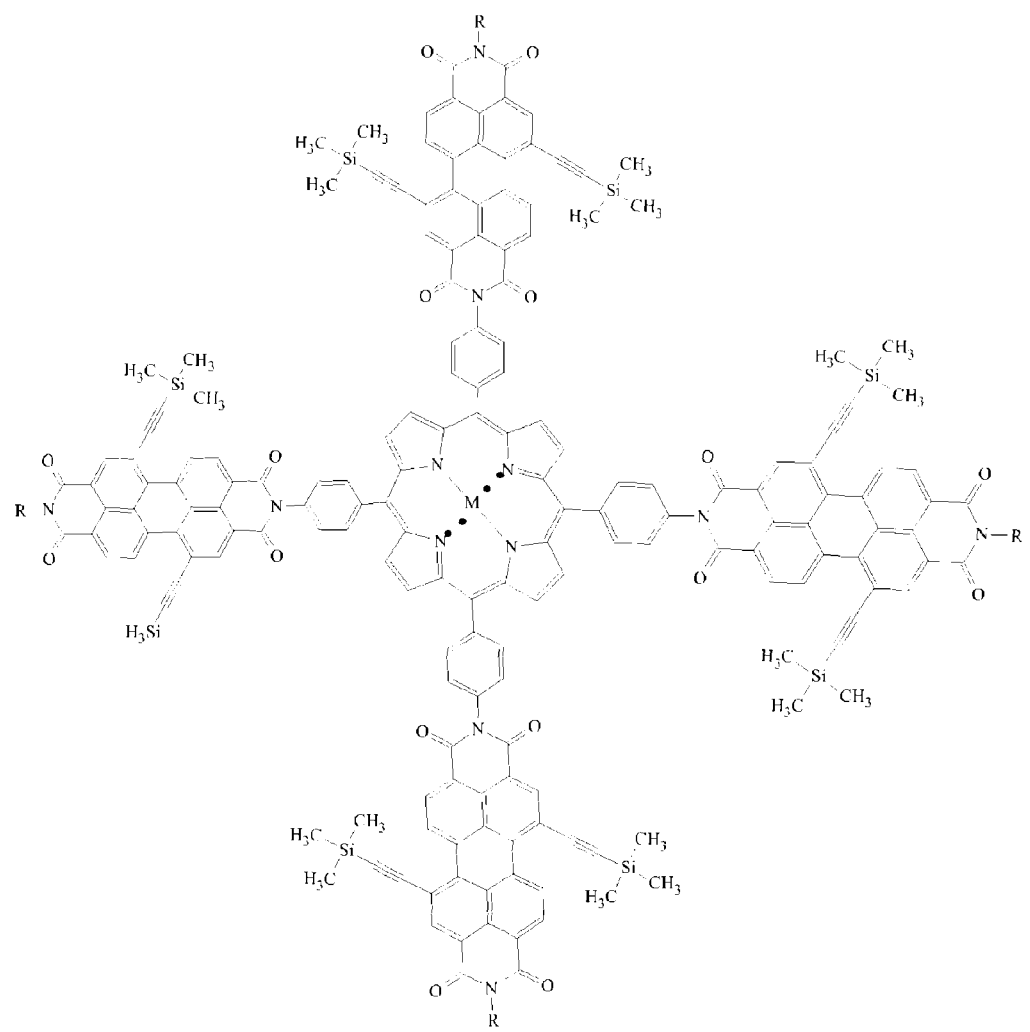
FIG. 6 shows first embodiment of an organic compound according to present invention.
Figure 7:
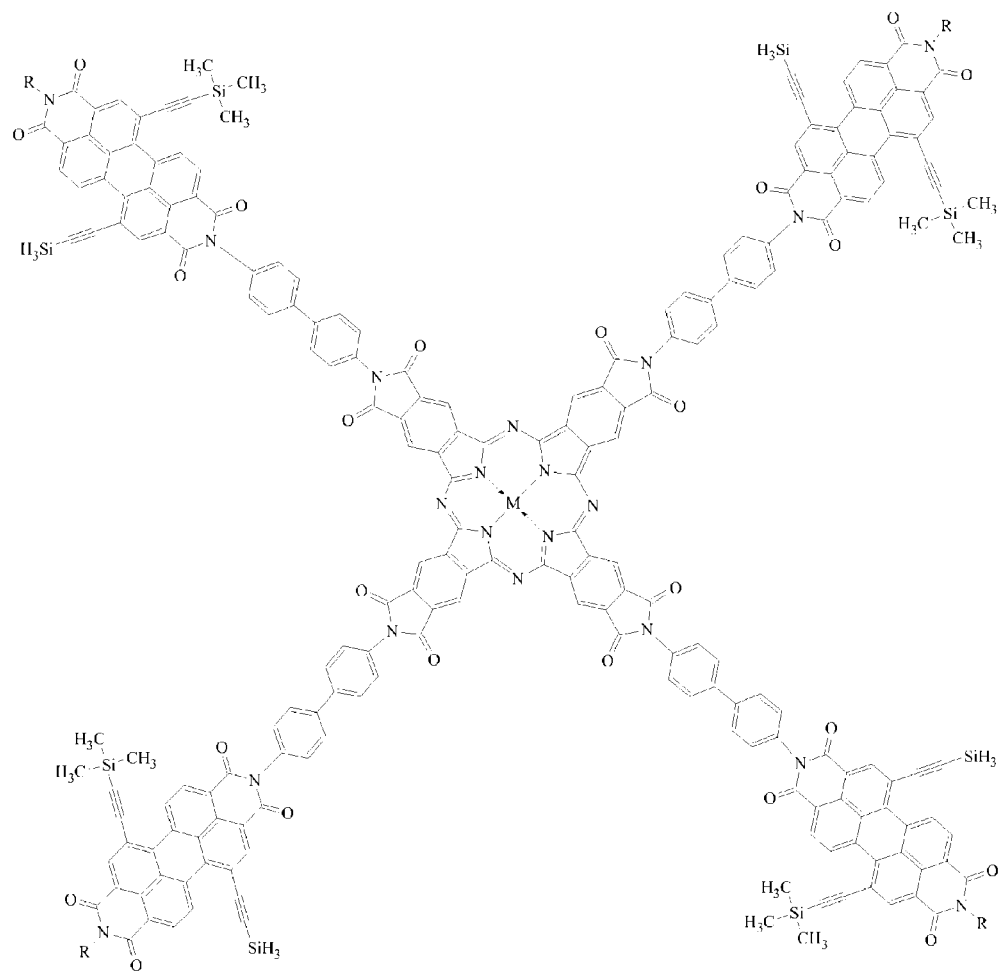
FIG. 7 shows second embodiment of an organic compound according to present invention.
Figure 8:
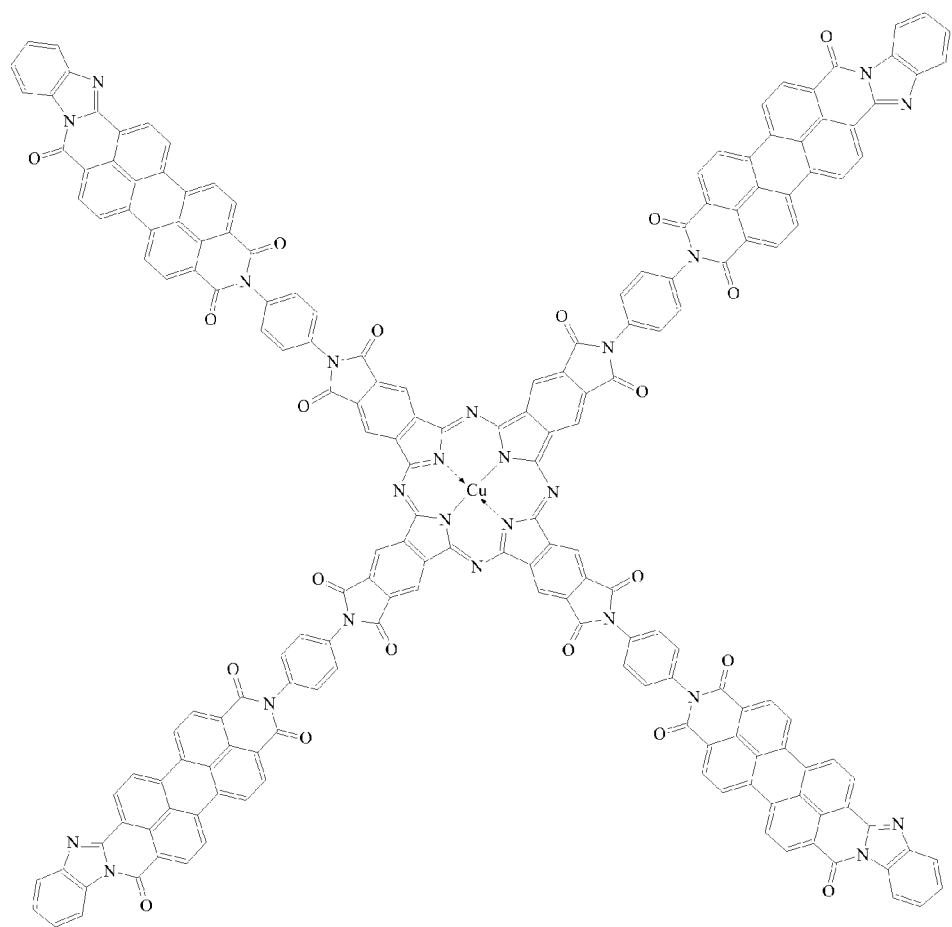
FIG. 8 shows third embodiment of an organic compound according to present invention.
Figure 9:
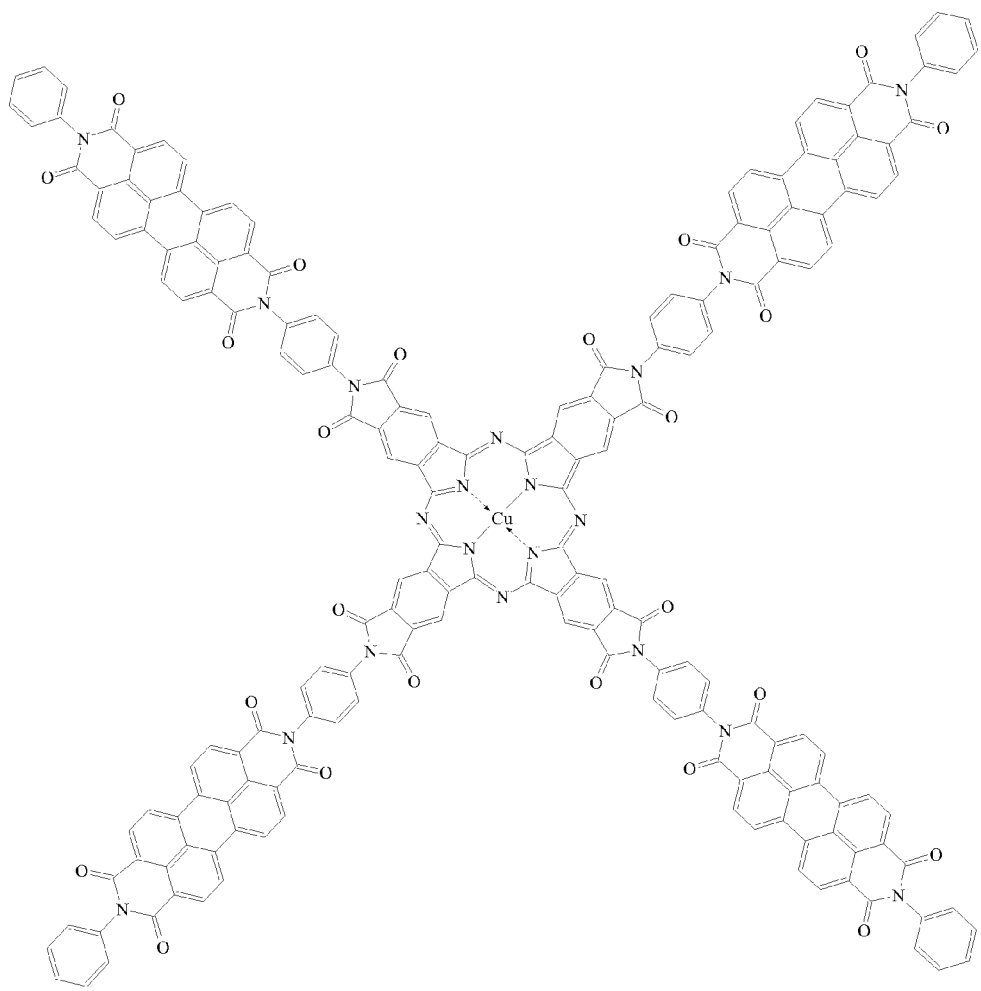
FIG. 9 shows fourth embodiment of an organic compound according to present invention.
Figure 10:
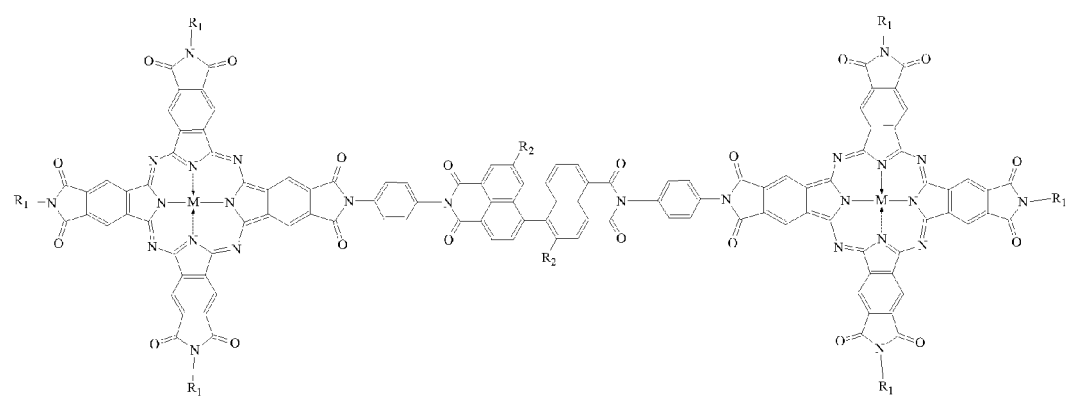
FIG. 10 shows fifth embodiment of an organic compound according to present invention.
Figure 11:
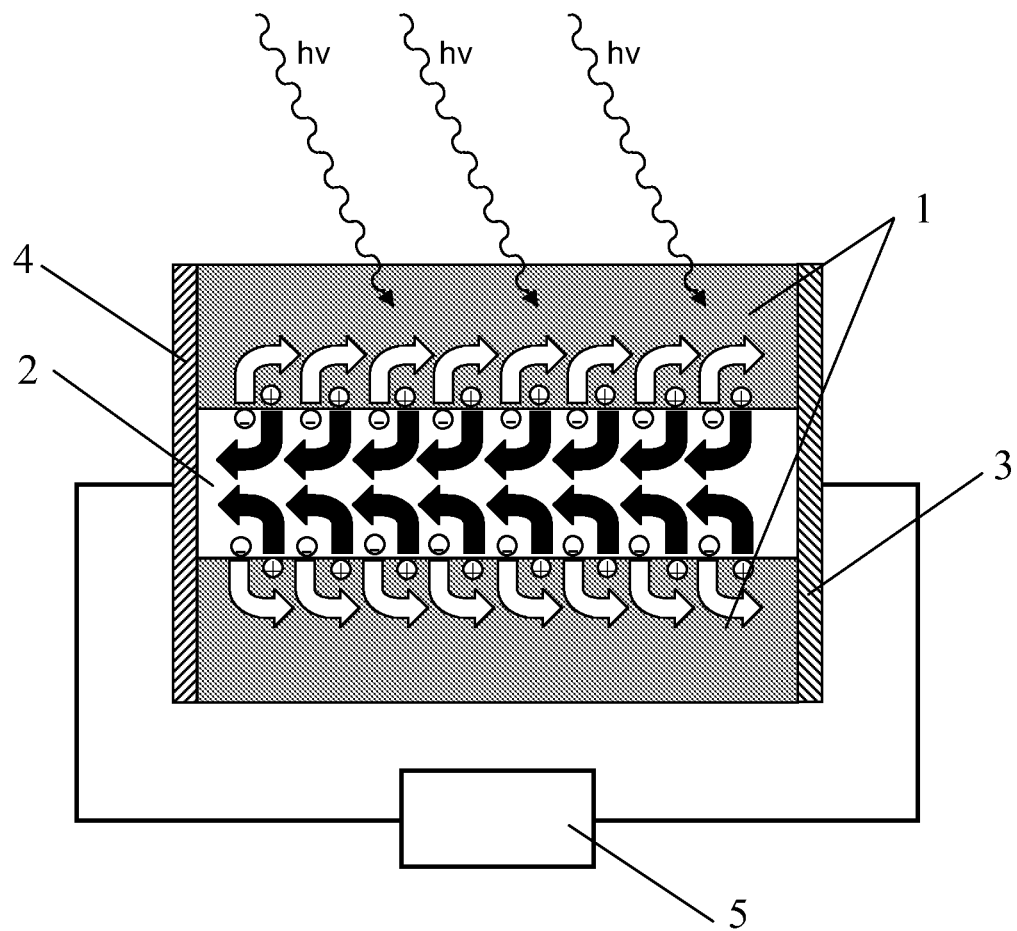
FIG. 11 shows the cross section of an organic photovoltaic device according to present invention.
Figure 12:
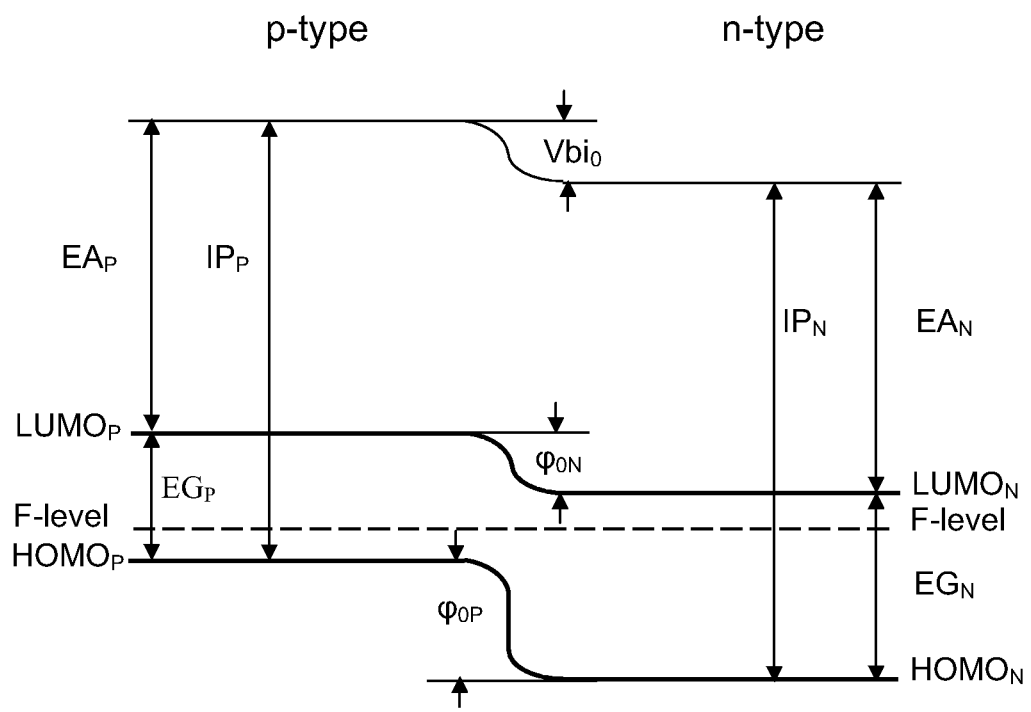
FIG. 12 is an energy band diagram of non-irradiated donor-bridge-acceptor system formed by p- and n-type molecular stacks connected by bridging groups.
Figure 13:
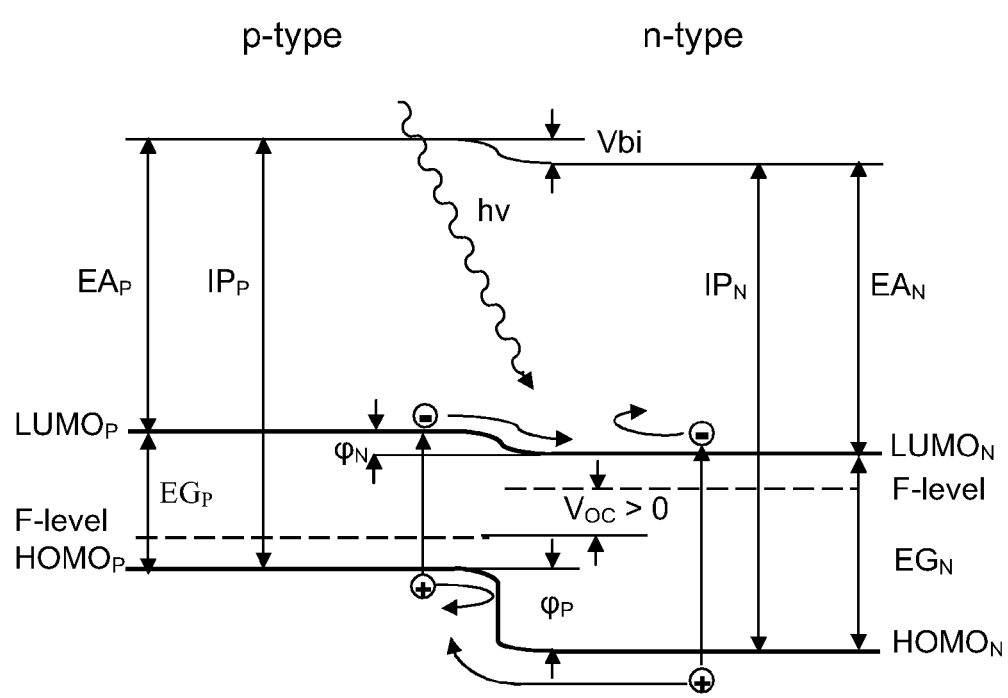
FIG. 13 is an energy band diagram of irradiated donor-bridge-acceptor system formed by p- and n-type molecular stacks connected by bridging groups.
Figure 14:
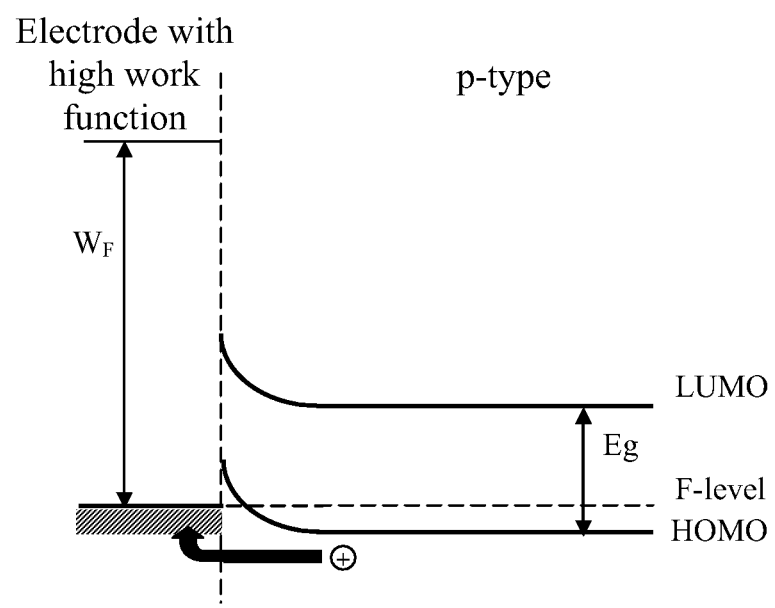
FIG. 14 is an energy band diagram of hole-harvesting contact.
Figure 15:
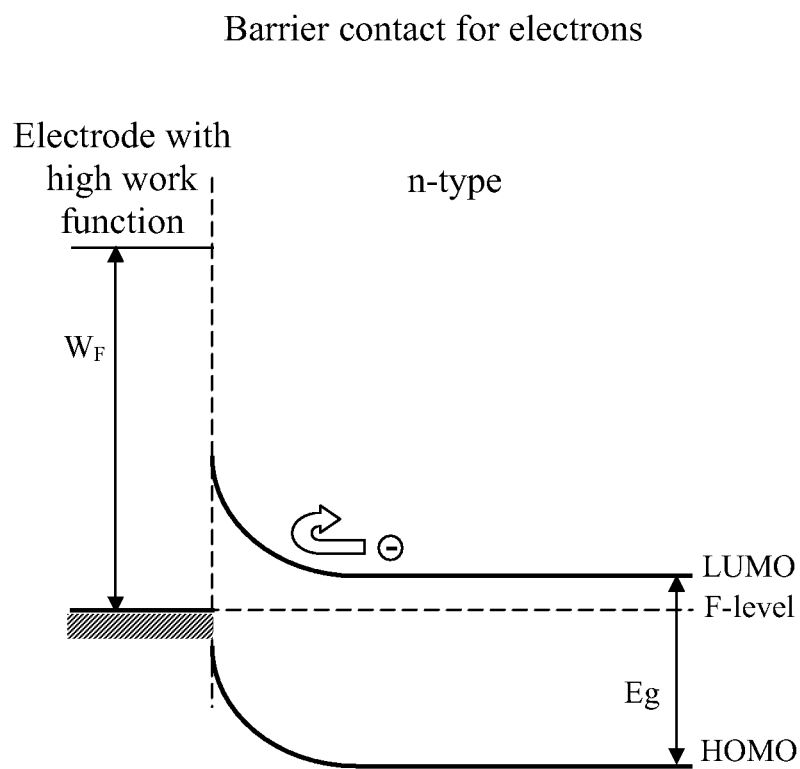
FIG. 15 is an energy band diagram of barrier contact for electron.
Figure 16:
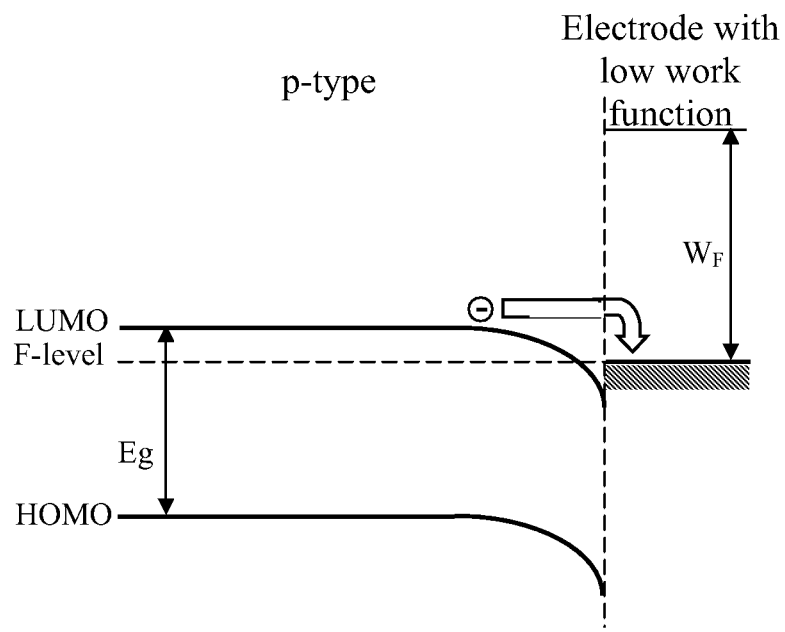
FIG. 16 is an energy band diagram of electron-harvesting contact.
Figure 17:
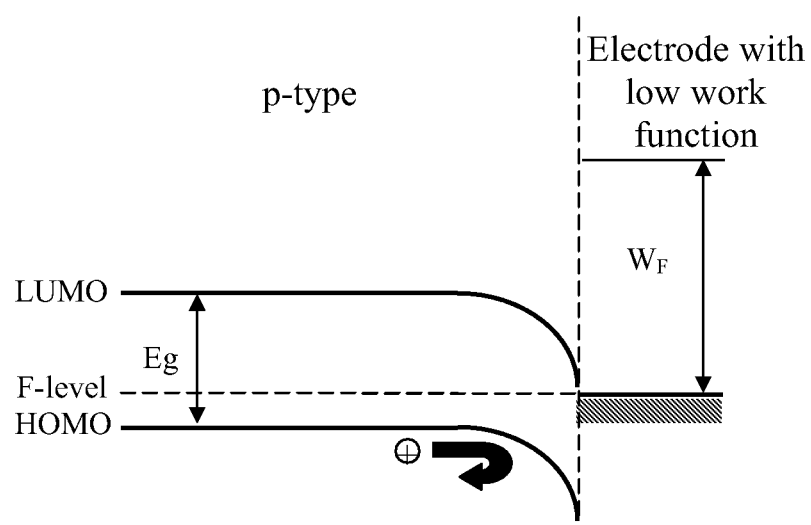
FIG. 17 is an energy band diagram of barrier contact for holes.
Figure 18:
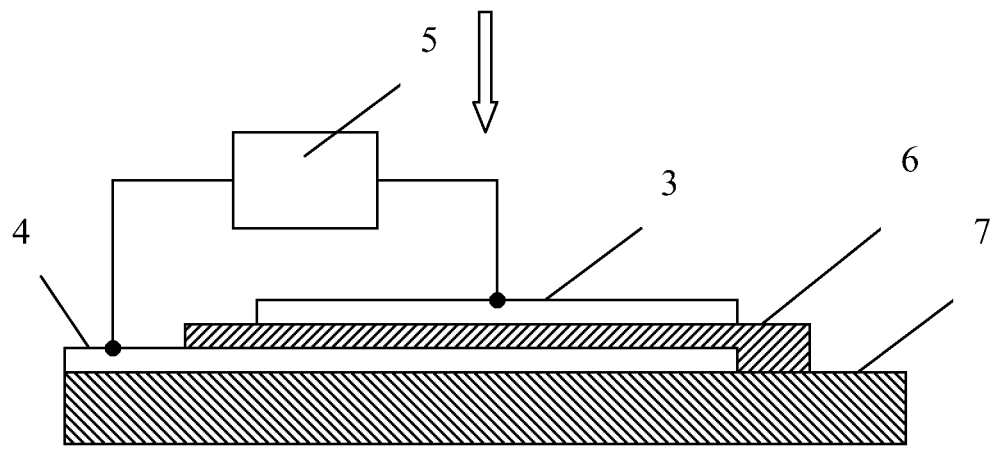
FIG. 18 is a schematic diagram of an organic photovoltaic device based on a structure with a photovoltaic organic layer with two contacts, which are located on the opposite surfaces of the photovoltaic layer.
Figure 19:
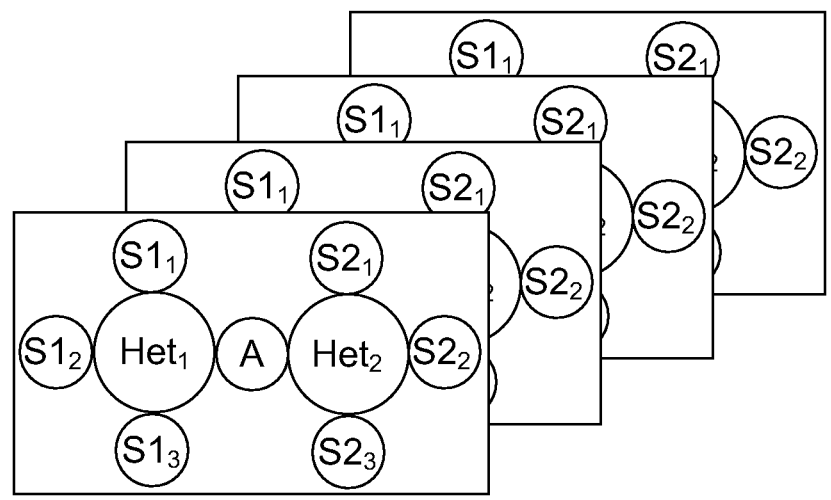
FIG. 19 schematically shows a top view of the molecular stack.
Figure 20:
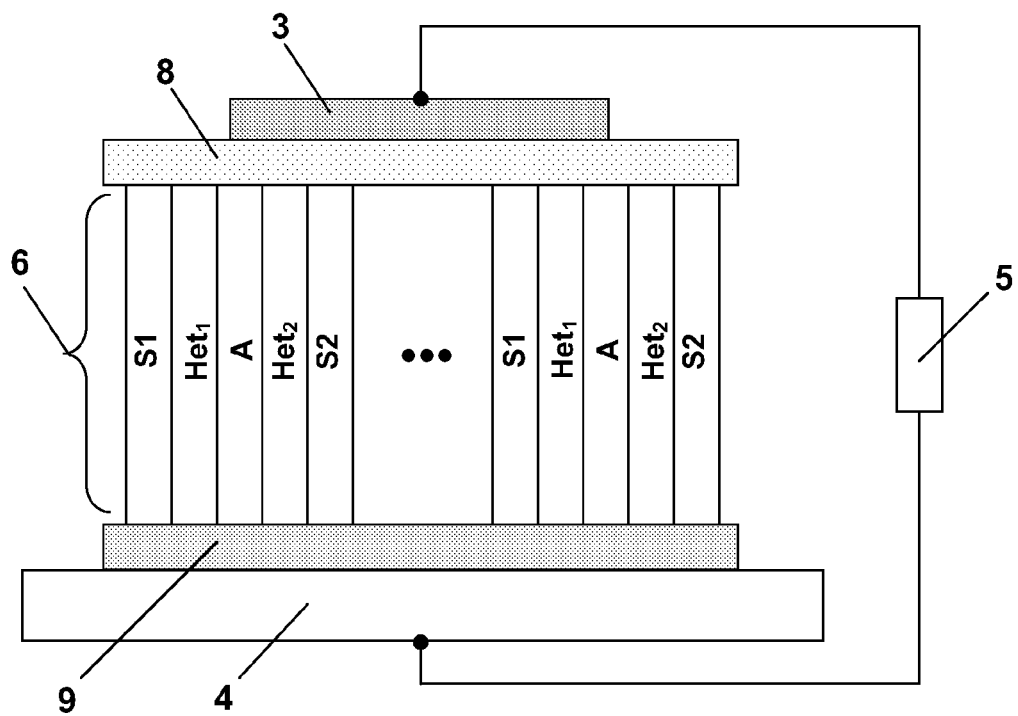
FIG. 20 schematically shows the disclosed organic photovoltaic device, based on photovoltaic layer comprising the molecular stacks oriented predominantly perpendicular to the its plane and located between the front electrode and the rear electrode.
Figure 21:
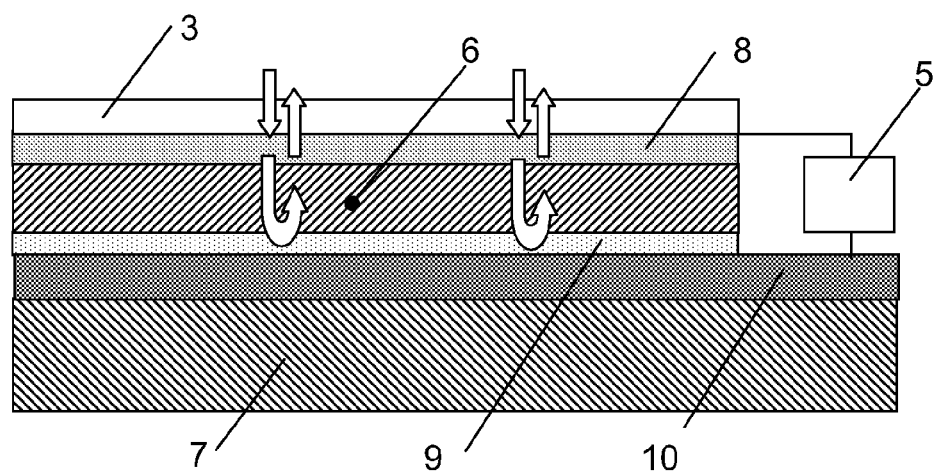
FIG. 21 schematically shows another embodiment of organic photovoltaic device with reflective electrode according present invention.
Figure 22:
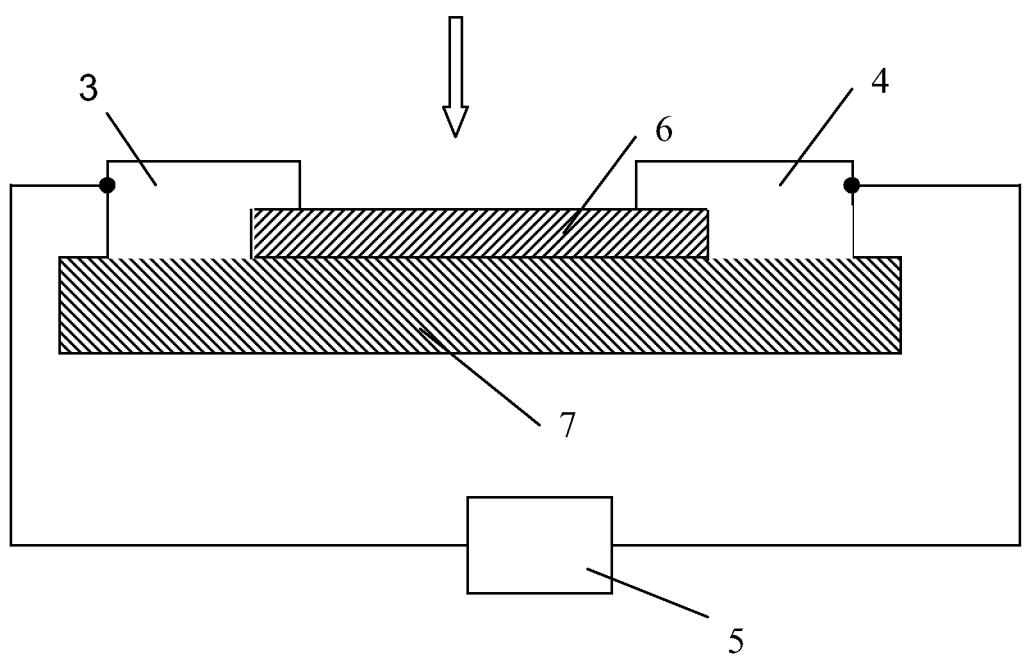
FIG. 22 schematically shows an organic photovoltaic device based on a single organic photovoltaic layer.

Another embodiment of the present invention, illustrated in FIG. 22, is based on a single organic photovoltaic layer (6). The photovoltaic layer has column-like supramolecules formed by means of π-π-interaction of single-type polycyclic molecular systems and having longitudinal axes oriented predominantly in the layer plane. At least a part of the front surface of said photovoltaic organic layer contacts with the first electrode (3) and at least a part of the same surface is in contact with the second electrode (4) as shown in FIG. 22. The column-like supramolecules arrange in photovoltaic layer (6) are predominantly aligned in direction from one electrode (3) to another one (4). The photovoltaic organic layer (6) is formed on substrate (7) and the electrodes are connected to a resistive load (5).

Figure 23:
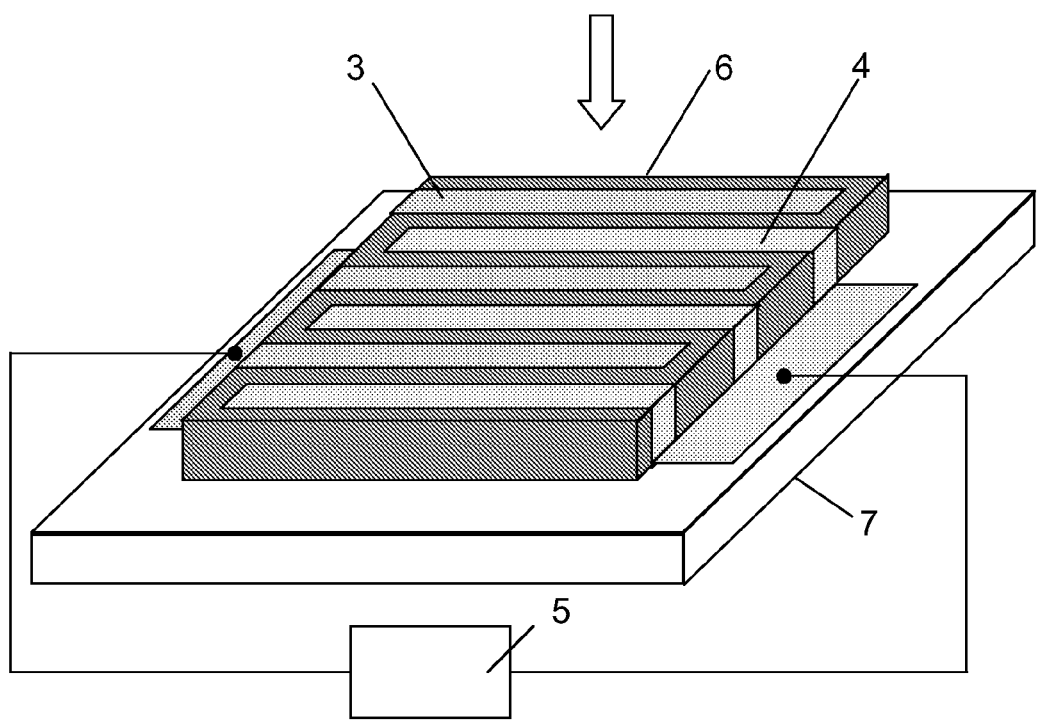
FIG. 23 shows an exemplary embodiment of the disclosed photovoltaic device with an interdigitated system of electrodes.

FIG. 23 shows an exemplary embodiment of the disclosed photovoltaic device with an interdigitated system of electrodes. This device comprises a photovoltaic layer (6) and two transparent electrodes (3) and (4). The photovoltaic layer (6) has the parallel column-like supramolecules oriented predominantly in the plane of the photovoltaic layer, the first electrode (3) is formed in grooves made on a part of one of the surfaces of said photovoltaic layer and the second electrode (4) is formed in grooves made on another part of the same surface of said photovoltaic layer. The photovoltaic layer is formed on a substrate (7) and the electrodes are connected to a resistive load (5).

Figure 24A:
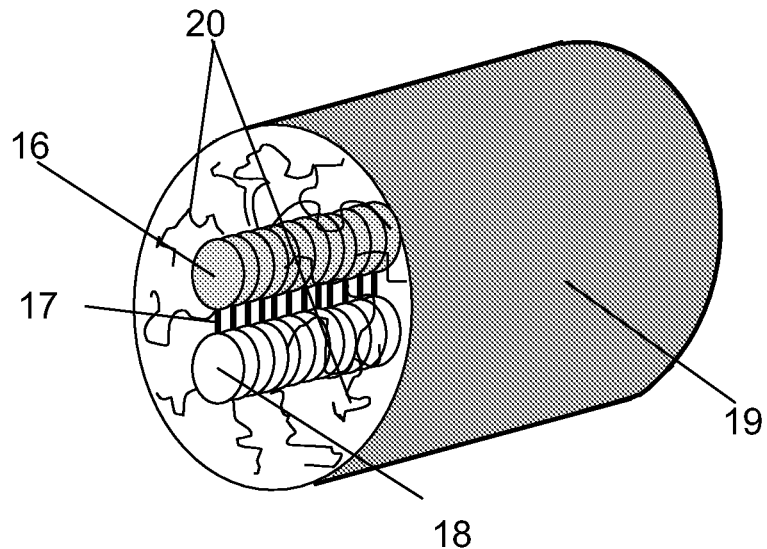
FIGS. 24a and 24b show schematically two embodiments of photovoltaic fibers according to present invention.
Figure 24B:
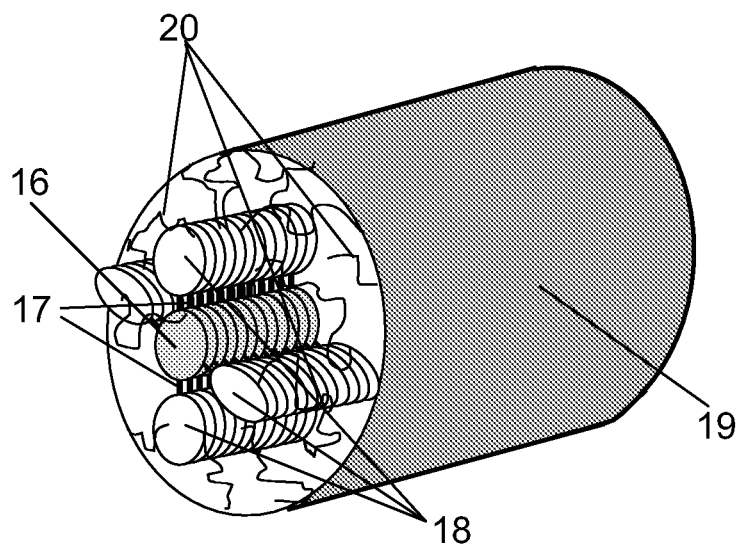

FIGS. 24a and 24b show schematically two embodiments of photovoltaic fibers according to present invention. The fibers comprise predominantly planar polycyclic molecular systems (Het$_1$) of first type (16), predominantly planar polycyclic molecular systems (Het$_2$) of second type (18) and bridging groups A (17) providing a lateral bond of the molecular systems Het$_1$ with the molecular systems Het$_2$ via strong chemical bonds. In one embodiment of the invention, the molecular systems Het$_1$ may be as electron acceptors, and the molecular systems Het$_2$ may be as electron donors. In another embodiment of the invention, the molecular systems Het$_2$ may be as electron acceptors, and the molecular systems Het$_1$ may be as electron donors. The donor-bridge-acceptor systems (Het$_1$-A-Het$_2$) form molecular stacks by means of π-π-interaction of the single-type polycyclic molecular systems providing current-conducting-paths with electron and hole conductivity. These stacks form a core of the photovoltaic fiber. Substituents and groups providing solubility of the organic compound (20) form an envelope (19) around the core. These envelopes electrically isolate the cores of the adjacent fibers.

Figure 25:
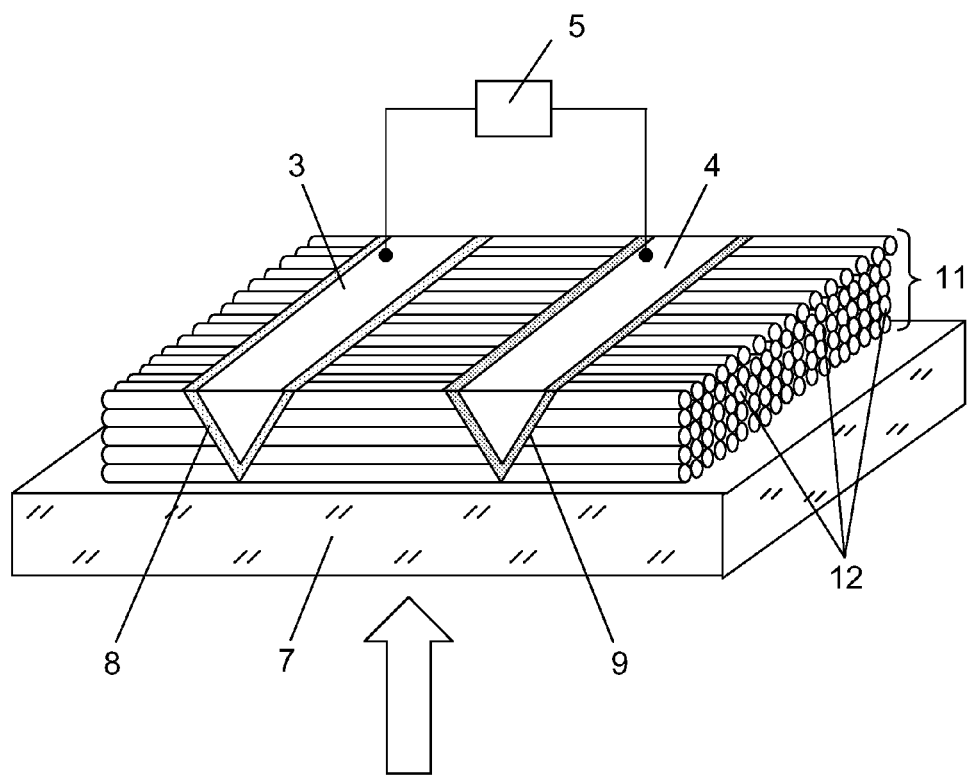
FIG. 25 shows a cell of disclosed photovoltaic device with an interdigitated system of electrodes shown in FIG. 23.
Figure 26:
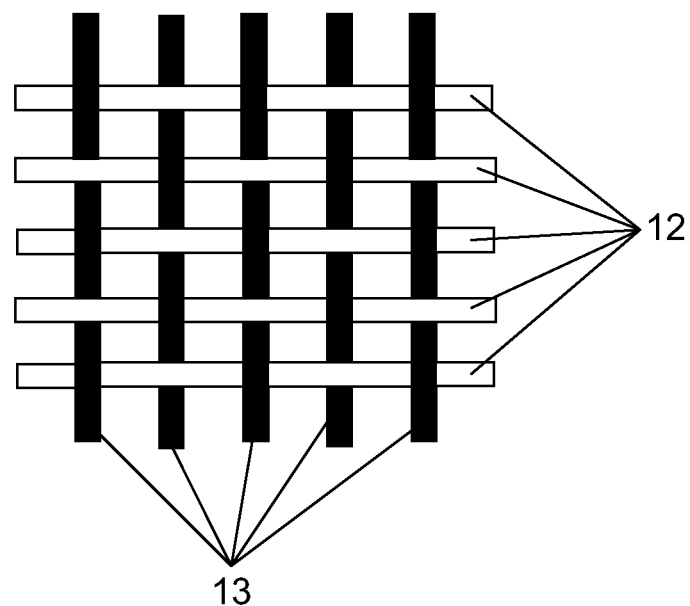
FIG. 26 shows a woven photovoltaic layer comprising photovoltaic fibers, wherein the photovoltaic fibers are arranged parallel to each other.

FIG. 25 shows a cell of disclosed photovoltaic device with an interdigitated system of electrodes shown in FIG. 23. In this embodiment of invention, the cell of disclosed device comprises a photovoltaic layer (11) made of photovoltaic fibers (12). Finger-like metal electrodes (3 and 4) are formed in grooves made in the photovoltaic layer. The grooves may be made with the help of chemical etching, ion-plasma etching, pressing, forcing, scratching, or by any other method known in prior art. Longitudinal axes of fibres and direction of electrodes are perpendicular each other. An electron acceptor layer (8) and an electron donor layer (9) are located in the grooves between the photovoltaic layer (11) and electrodes (3 and 4), respectively. The photovoltaic layer (11) is formed on a substrate (7) and the electrodes are connected to a resistive load (5). In another embodiment of the disclosed device, the photovoltaic layer is a woven photovoltaic layer comprising photovoltaic fibers, wherein the photovoltaic fibers (12) according to the present invention are arranged predominantly parallel to each other and the photovoltiac fibers are fixed in place with the non-photovoltaic fibers (13) (see FIG. 26).

Figure 27:
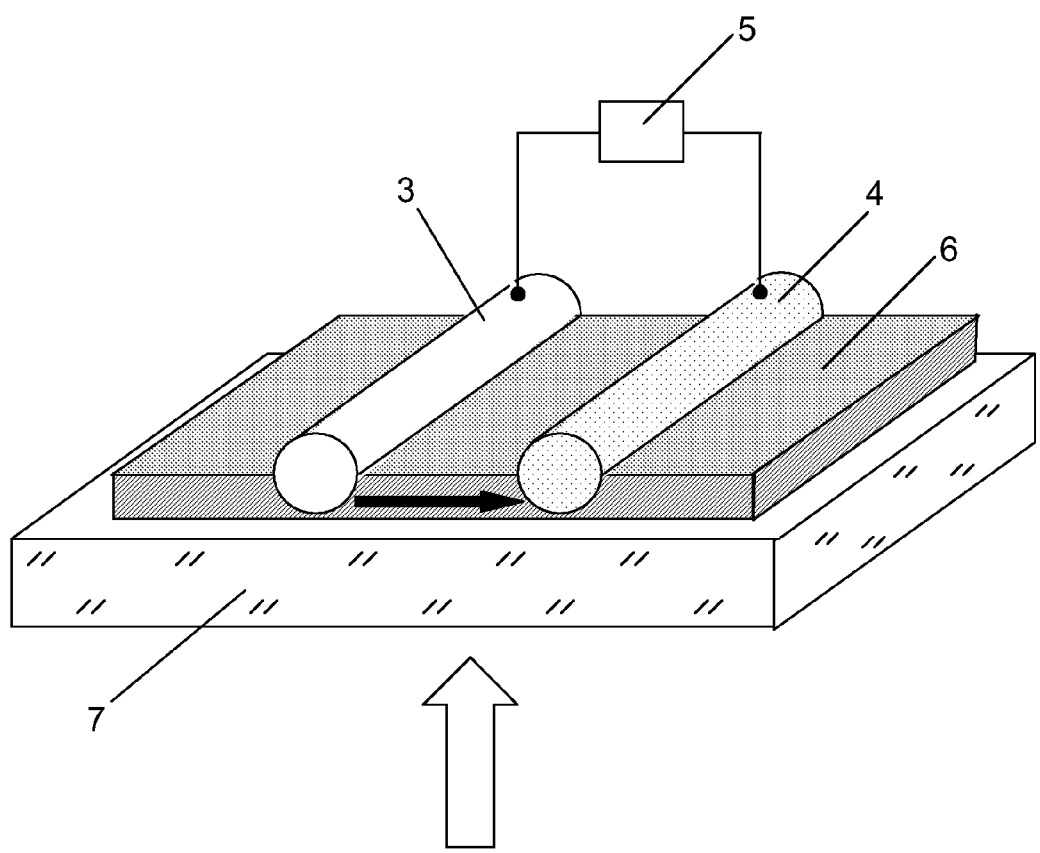
FIG. 27 shows another embodiment of cell of photovoltaic device.

FIG. 27 shows another embodiment of cell of photovoltaic device. In this embodiment of invention, the cell of disclosed device comprises a photovoltaic layer (6) and finger-like metal electrodes (3 and 4). These electrodes are forced down into the photovoltaic layer. The first electrode (3) is made of material with a work function providing a hole-harvesting contact and a barrier contact for electrons and the second electrode (4) is made of material with a work function providing a barrier contact for holes and an electron-harvesting contact. The photovoltaic layer (6) is formed so that longitudinal axes of column-like supramolecules were perpendicular to a direction of the electrodes. The photovoltaic layer (6) is formed on a substrate (7) and the electrodes are connected to a resistive load (5). The black arrow shows an alignment direction of the organic compound on the substrate.

Figure 28:
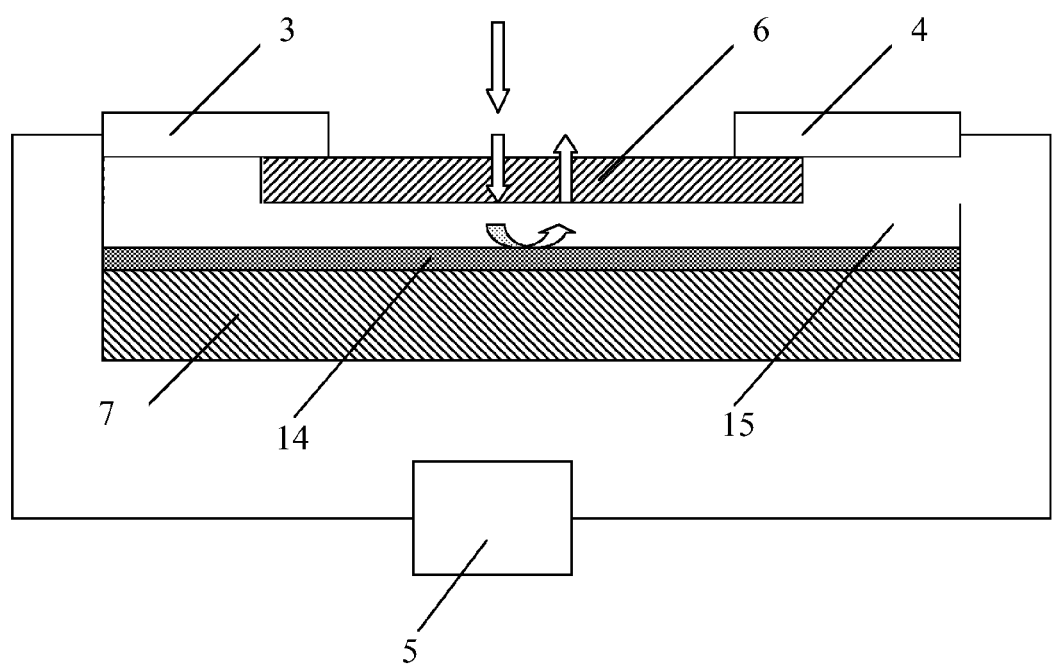
FIG. 28 shows yet another embodiment of disclosed organic photosensitive optoelectronic device with an additional reflective a retarder layers.

In yet another embodiment of disclosed organic photosensitive optoelectronic device is illustrated in FIG. 28. This device comprises a photovoltaic layer (6) and two electrodes (3) and (4) formed on one surface of the photovoltaic layer. First electrode (3) is made of material with work function providing a hole-harvesting contact and a barrier contact for electrons and the second electrode (4) is made of material with work function providing a barrier contact for holes and an electron-harvesting contact, while a retarder layer (15) and an additional reflective layer (14) with a reflection coefficient of not less than 95% for the incident radiation are formed on the another surface of the photoelectric layer. The entire multilayer structure is formed on a substrate (7) and the electrodes are connected to a resistive load (5). In this structure, the incident electromagnetic radiation doubly passes through the active photoelectric layer of the device structure thus increasing the efficiency of conversion. While the electromagnetic radiation incident on layer (6) is nonpolarized, the radiation transmitter through photovoltaic layer in one direction will be partly polarized. Being reflected from the reflective layer, the radiation polarized parallel to the transmission axis of the photovoltaic layer (6) will not be repeatedly absorbed in this layer on the second passage. In order to avoid this and increase the conversion efficiency of said device, it is necessary to rotate the polarization vector 90°. To this end, an additional retarder layer (15) is introduced between a photovoltaic layer (6) and a reflective layer (14). The thickness and optical anisotropy of this retarder are selected so as to ensure a 45°-rotation of the polarization vector of the transmitted radiation. Since the electromagnetic radiation double-passes through this layer, the resulting polarization rotation amounts to 90°. Thus, the combination of retarder and reflective layer provides for a more complete use of the incident electromagnetic radiation and ensures an increase in the photovoltaic conversion efficiency of this embodiment.

The solid photovoltaic layer may be produced by the following method, which involves application on a substrate of a solution of one organic compound, or a combination of such organic compounds, of the general structural formula

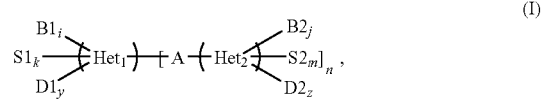

(I)

and drying with the formation of a photovoltaic layer. Here, $Het_1$ is a predominantly planar polycyclic molecular system of first type; $Het_2$ is a predominantly planar polycyclic molecular system of second type; A is a bridging group providing a lateral bond of the molecular system $Het_1$ with the molecular system $Het_2$ via strong chemical bonds; n is 1, 2, 3, 4, 5, 6, 7 or 8; B1 and B2 are binding groups; i is 0, 1, 2, 3, 4, 5, 6, 7 or 8; j is 0, 1, 2, 3, 4, 5, 6, 7 or 8; S1 and S2 are groups providing solubility of the organic compound; k is 0, 1, 2, 3, 4, 5, 6, 7 or 8; m is 0, 1, 2, 3, 4, 5, 6, 7 or 8; D1 and D2 are substituents independently selected from a list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$; y is 0, 1, 2, 3, 4, 5, 6, 7 or 8; and z is 0, 1, 2, 3, 4, 5, 6, 7 or 8. Said organic compound is capable of forming supramolecules. The molecular system $Het_1$, the bridging group A, and the molecular system $Het_2$ are capable of forming a donor-bridge-acceptor system providing dissociation of excited electron-hole pairs. The solution may absorb electromagnetic radiation only in a part of wavelength range from 400 to 3000 nm. This part of spectral range will be called as subrange. This subrange may be determined experimentally for each particular solution. Thus, such subrange of absorption of the electromagnetic radiation can be considered as the predetermined subrange. In one embodiment of the disclosed method, said solution is based on water and/or water-miscible solvents. In another embodiment of the disclosed method, at least one of the groups providing a solubility of the organic compound in water and/or water-miscible solvents is selected from the list comprising $COO^-$, $SO_3^-$, $HPO_3^-$, and $PO_3^{2-}$ and any combination thereof. In yet another embodiment of the disclosed method, the photovoltaic layer produced from water solutions has polycyclic molecular systems with planes oriented predominantly perpendicularly to the substrate plane.

In one embodiment of the disclosed method, said solution is based on organic solvent. In this embodiment of the disclosed method, the organic solvent is selected from the list comprising benzol, toluene, xylenes, acetone, acetic acid, methylethylketone, hydrocarbons, chloroform, carbontetrachloride, dichlorethane, methylenechloride, chlorobenzol, alcohols, nitromethan, acetonitrile, dimethylforamide, 1,4-dioxane or any combination thereof. In another embodiment of the disclosed method, at least one of the groups providing a solubility of the organic compound in organic solvent is amide of acid residue independently selected from the list comprising $CONR_1R_2$, $CONHCONH_2$, $SO_2NR_1R_2$, and any combination thereof, were $R_1,R_2$ independently selected from H, alkyl or aryl. The alkyls may be selected from the list comprising methyl, ethyl, propyl, butyl, i-butyl, t-butyl and aryls may be selected from the list comprising phenyl, benzyl, naphthyl. The examples of alkyls and aryls serve to illustrate the invention without limiting it. In yet another embodiment of the disclosed method, at least one of the groups providing a solubility of the organic compound in organic solvent is alkyl. In still another embodiment of the disclosed method, the photovoltaic layer produced from organic solutions has polycyclic molecular systems with planes oriented predominantly parallel to the substrate plane.

In one embodiment of the disclosed method, said solution absorbs electromagnetic radiation within a wavelength range from 400 to 700 nm. In one embodiment of the disclosed method, said predominantly planar polycyclic molecular system is a partially or completely conjugated. In still another embodiment of the disclosed method, said polycyclic molecular system comprises the hetero-atoms selected from the list comprising nitrogen, oxygen, sulfur, and any combination thereof. In yet another embodiment of the disclosed method, at least one of the binding group is selected from the list comprising the hetero-atoms, COOH, $SO_3H$, $H_2PO_3$, NH, $NH_2$, NHR, $NR_2$, and any combination thereof, where radical R is alkyl or aryl.

The examples of polycyclic molecular systems of a general structural formula corresponding to structures 1-29 shown above in Tables 1-3 serve to illustrate the disclosed method without limiting it. In still another embodiment of the disclosed method for obtaining semiconductor crystal films, the planar polycyclic molecular system comprises phthalocyanine fragments. Some examples of such planar polycyclic molecular systems comprising phthalocyanine fragments having a general structural formula from the group comprising structures 1-6 are given in Table 1. In another embodiment of the disclosed method, the planar polycyclic molecular system comprises rylene fragments. Some examples of such planar polycyclic molecular systems comprising rylene fragments having a general structural formula from the group comprising structures 7-27 are given in Table 2. In another embodiment of the disclosed method, the planar polycyclic molecular system comprises naphthalene fragments. Some examples of such polycyclic molecular systems having a general structural formula from the group comprising structures 28-29 are given in Table 3.

In one another embodiment of the disclosed method, the applied solution layer is dried in airflow. In another embodiment of the disclosed method, the substrate is pretreated to provide surface hydrophilization before application of said solution layer. In yet another embodiment of the present invention, the disclosed method further comprises the stage of treatment of the photovoltaic layer with a solution of any water-soluble inorganic salt with a cation selected from the group comprising $Ba^{++}$, $Zn^{++}$, $Sr^{++}$, $Ca^{++}$, $Mg^{++}$, and any combination thereof. The polyvalent counterions ($Ba^{++}$, $Ca^{++}$, $Mg^{++}$, $Sr^{++}$, $Zn^{++}$) are used for stabilization of the organic compounds and provide their insolubility. In one embodiment of the disclosed method, said photovoltaic layer is formed by planar polycyclic molecular systems of two or more types ensuring the absorption of electromagnetic radiation in different subranges within a wavelength range from 400 to 3000 nm.

In one embodiment of the disclosed method, said applied solution is isotropic. In another embodiment of the disclosed method, said solution is a lyotropic liquid crystal solution. In one embodiment of the method, the application of said lyotropic liquid crystal solution on the substrate is accompanied or followed by an orienting action upon this solution. In another embodiment of the method, the application stage is carried out using a spray-coating. In yet another embodiment of the disclosed method, the cycle of the technological operations of solution application and drying is repeated two or more times, and sequential photovoltaic layers are formed using solutions absorbing electromagnetic radiation in predefined spectral subranges, which can be either the same or different for various photovoltaic layers.

EXAMPLE 1

The example describes a method of synthesis of porphyrin-(phenyl-perylene diimide)4-compound (TPP-PDI4) represented by the general structural formula III and comprising fragments represented by structural formulas 6 and 9 (Tables 1 and 2),

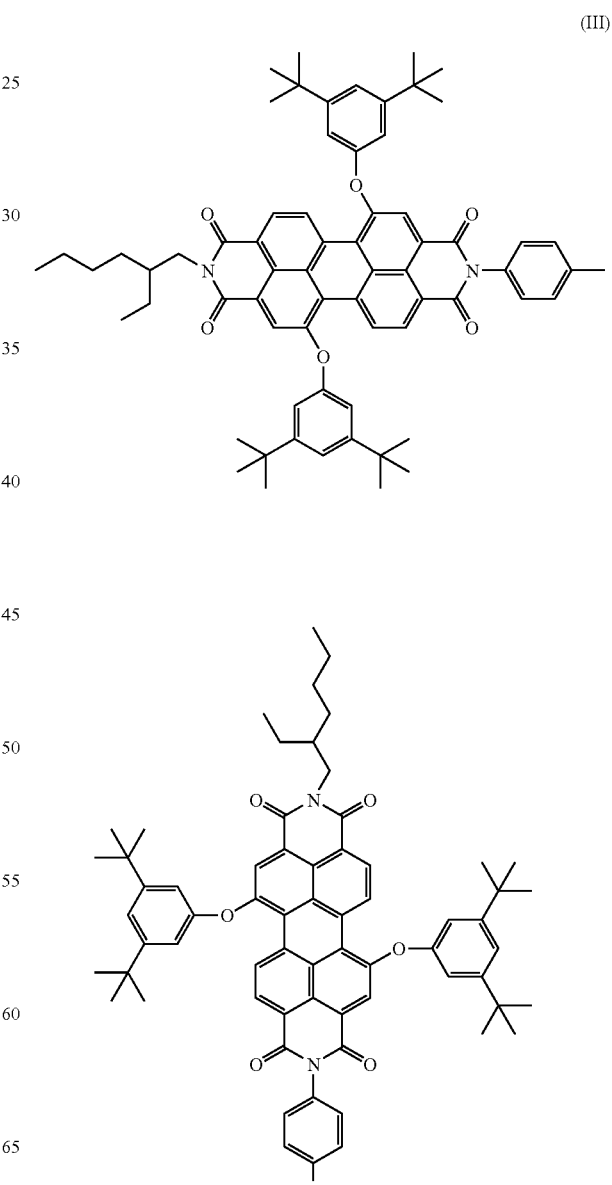

(III)

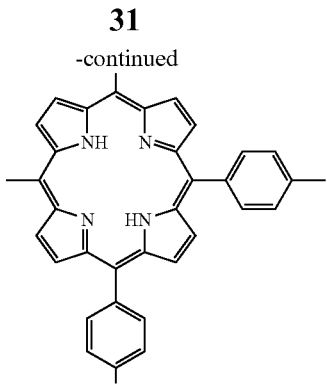

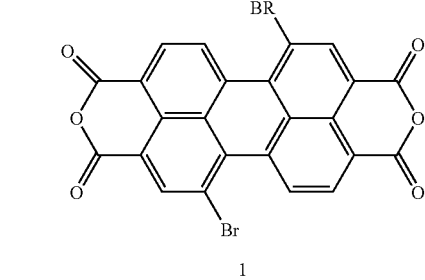

(30)

For this purpose 3,4:9,10-perylenetetracarboxylic dianhydride (28.52 g, 72.7 mmol) was added to 420 ml concentrated sulfuric acid and stirred at 55° C. for 24 hours. Iodine (0.685 g, 2.70 mmol) was added to the reaction mixture and stirred for additional 5 hours at 55° C. Bromine (8.3 ml, 162 mmol) was added dropwise to the reaction flask over 1 hour and stirred for 24 hours at 85° C. The excess bromine was then displaced with the nitrogen gas N2. Water (66 ml) was added dropwise to the cooled mixture and the precipitate was filtered off. The crude product was washed with 220 ml 86% $H_2SO_4$ followed by water and this procedure was repeated two times to produce the crude product (32.32 g, 81%). This product was used further without any purification. M.S.: 549.0 (calcd. 550.11).

In the second step a synthesis of 1,7-(3',5'-di-t-butylphenoxy)perylene-3,4:9,10-tetracarboxydianhydride (PDA) represented by the general structural formula 31 was carried out.

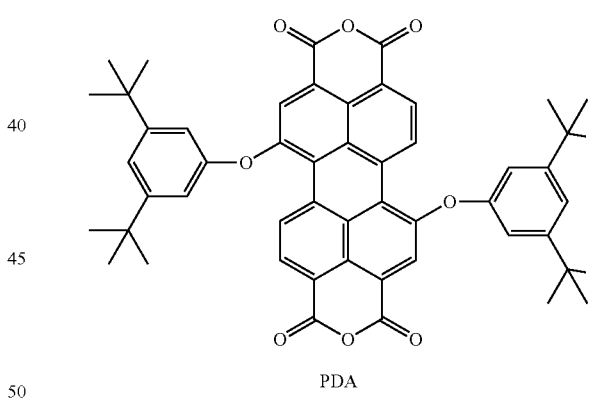

(31)

PDA

For this purpose 1,7-Dibromoperylene-3,4,:9,10-tetracarboxydianhydride (0.89 g, 1.61 mmol), 3,5-di-tert-butylphenol (1.0 g, 4.85 mmol), and Cs2CO3 (1.1 g, 3.38 mmol) were placed into two-neck flask equipped with magnetic stirrer bar, air condenser, and argon outlet. Then DMF (15 mL) was added and the resulting suspension was refluxed with the intensive stirring for 1.5 hours. An initially red suspension turned to a deep violet one. Reaction mixture was cooled to room temperature and acetic acid (10 mL) was added. The formed precipitate was stirred overnight at room temperature, filtered off, washed with ice cold acetic acid (40 mL) and hot MeOH (40 mL), dried under vacuum for 6 hours at 60° C. to give pure product 1.2 g (87%). M.S.: 799.9 (calcd. 800.3). 1H NMR (CDCl3) δ: 9.69 (d, J=8.4, Hz, 2H), 8.68 (d, J=8.4 Hz, 2H), 8.37 (s, 2H), 7.42 (t, J=1.7, 2H), 7.03 (d, J=1.7, 4H), 1.35 (s, 36H).

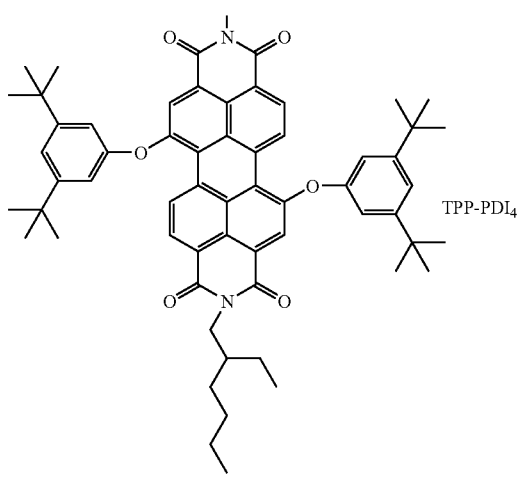

TPP-PDI4

Said method comprises the following steps.

In the first step a synthesis of 1,7-dibromoperylene-3,4:9,10-tetracarboxydianhydride represented by the general structural formula 30 was carried out:

In the third step a synthesis of N-(2-ethylhexyl)-1,7-(3',5'-di-t-butylphenoxy)perylene-3,4-dicarboxyanhydride-9,10-dicarboximide (PIA) represented by the general structural formula 32 was carried out:

(32)

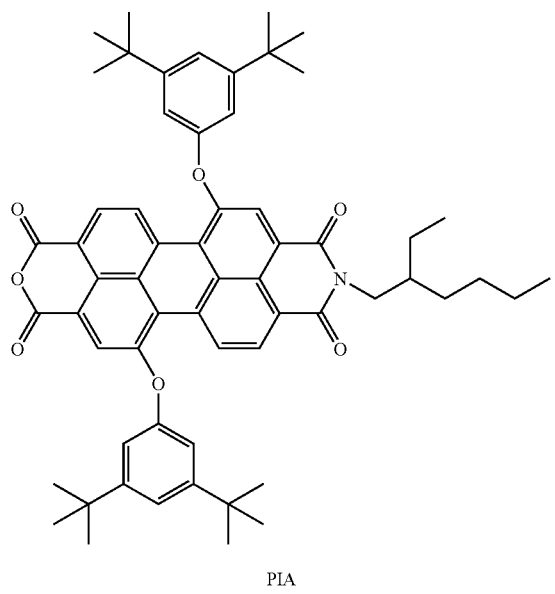

PIA

For this purpose 1,7-(3'5'-Di-t-butylphenoxy)perylene-3,4,:9,10-tetracarboxydianhydride (PIA) (0.85 g, 1.06 mmol), imidazole (0.85 g, 12.4 mmol) were placed into a three-neck flask equipped with magnetic stirrer bar, air condenser, argon inlet tube, and dropping funnel. Chloroform (250 mL, freshly distilled from $CaH_2$) was added. The resulting suspension was refluxed with the intensive stirring for 1 hour and 2-ethylhexylamine (0.136 g, 1.06 mmol) in chloroform (8 mL) was added dropwise for 1 hour, followed by 5 drops of CF3COOH. Reaction mixture was refluxed for 3 days, cooled down, the solvent was removed under reduced vacuum. The product was purified on column chromatography on silica gel (eluent CHCl3-hexane 4:1) to produce an analytically pure monoanhydride (PDI) as red solid material (Yield: 0.24 g, 24%). M.S.: 911.50 (calcd. 911.48). 1H NMR (CDCl3) δ: 9.70 (d, J=2.6 Hz, 1H), 9.68 (d, J=2.6 Hz, 1H), 8.64 (d, J=5.03 Hz, 1H), 8.62 (d, J=5.03 Hz, 1H), 8.36 (s, 1H), 8.33 (s, 1H), 7.38 (t, J=1.7 Hz, 1H), 7.37 (t, J=1.7 Hz, 1H), 7.027 (d, J=1.7 Hz, 2H), 7.02 (d, J=1.7 Hz, 2H), 4.10 (m, 2H), 1.98 (m, 1H), 1.34 (m, 6H), 1.21 (s, 18H), 1.20 (s, 18H), 0.91 (m, 8H).

In the last step a final assembling of porphyrin-(phenyl-perylene diimide)4-compound (TPP-PDI4) represented by the general structural formula III was carried out. For this purpose 5,10,15,20-Tetrakis(p-aminophenyl)porphyrin (50 mg, 0.074 mmol), PIA (334 mg, 0.36 mmol) and imidazole (3.0 g) are added to 10 ml of pyridine. The reaction mixture was heated to reflux under dry nitrogen for 2 days with stirring. The reaction is slow (monitored by MALDI) and additional PIA (252 mg, 0.28 mmol) was added. The reaction mixture was refluxed for another 2 days and then diluted with chloroform, washed one time with 2N hydrochloric acid, 2 times with water, dried over anhydrous potassium carbonate, and the solvent stripped on a rotary evaporator. The residue is column chromatographed on silica gel with chloroform to afford TPP-PDI4 (130 mg, 40%). Mass spectrum: 4245 (calc. 4245) 1H NMR δ (CDCl3) 9.8 (broad, 4H), 9.7 (broad 4H), 8.8 (broad, 4H), 8.6 (broad, 4H), 8.5 (broad, 4H), 8.2 (broad, 4H), 7.7 (broad, 4H), 7.5 (broad, 4H), 7.47 (broad, 8H), 7.39 (broad, 8H), 7.15 (broad, 24H), 4.1 (m, 8H), 2.7 (s, 12H), 2.7 (broad, 24H), 2.0 (broad, 4H), 1.3 (broad, 24H), 1.4 (broad, 144H), 0.8 (broad, 32H). The synthesis of TPP-PDI4 have been performed according with known literature procedures (see, 1.) van der Boom, T.; Hayes, R. T.; Zhao, Y.; Bushard, P. J.; Weiss, E. A.; Wasielewski, M. R. J. Am. Chem. Soc. 2002, 124, 9582; 2.) M. J. Ahrens, L. E. Sinks, B. Rybtchinski, W. Liu, B. A. Jones, J. M. Giaimo, A. V. Gusev, A. J. Goshe, D. M. Tiede, M. R. Wasielewski, J. Am. Chem. Soc., 2004, 126, 8284).

EXAMPLE 2

Figure 29:
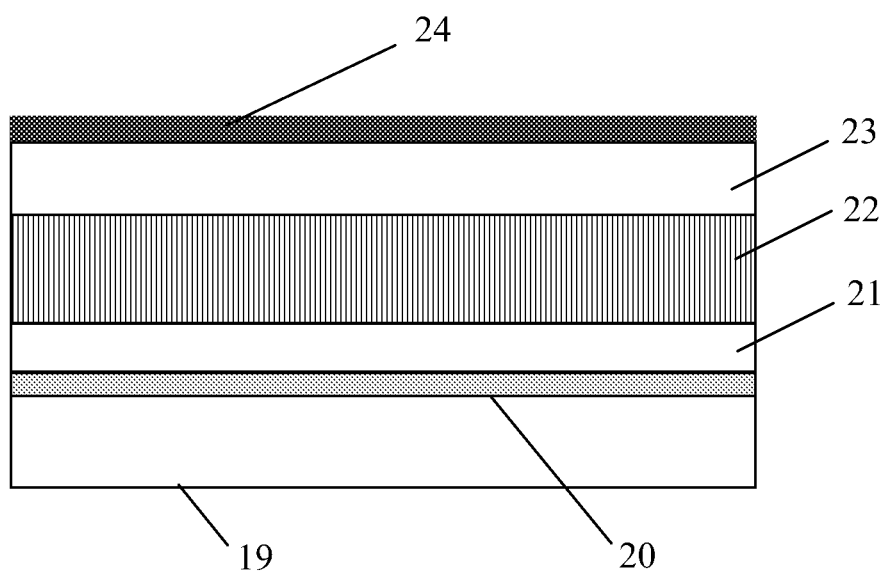
FIG. 29 shows schematically another embodiment of the organic photovoltaic device based on the photovoltaic layer according to the present invention.

The second example describes the organic photovoltaic device based on the photovoltaic layer according to the present invention. The schematic view of the device is shown in FIG. 29. The photovoltaic layer comprises predominantly planar organic compound and is disposed between the first and second electrodes. The first electrode comprises ITO layer and a layer made of PEDOT:PSS represented by the general structural formula (IV) and contacting the photovoltaic layer. The second electrode comprises aluminum layer and a layer made of LiF contacting to the photovoltaic layer. The first electrode provides a hole-harvesting contact and a barrier contact for electrons, and the second electrode provides a barrier contact for holes and an electron-harvesting contact.

(IV)

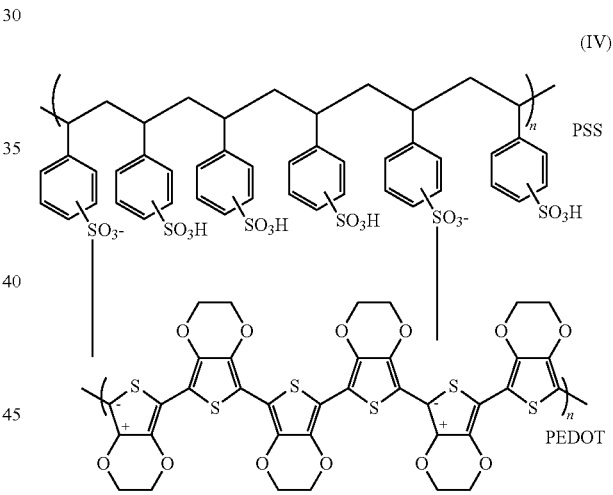

The glass/ITO substrates were pre-cleaned with the following standard chemical treatment procedure.
1. Ultrasonic bath with the special surfactant at T=20-40° C. for 20 min.
2. Soak in water and wash with running water for 10 min.
3. Ultrasonic bath with water solution of NaOH (w/w 10%)+KMnO4 (w/w 0.1%) for 30 min;
4. Soak in water and wash with running water for 10 min.
5. Thorough rinsing with deionized water (water conductivity ~5 μCm/cm).
6. Compressed air stream drying.
7. Treatment with oxygen plasma (high frequency, 1 min, 500 Watts).

Then PEDOT:PSS was spin-coated at 3000 rpm from 1.3% water solution. In order to delete residual water and form the fully bonded phase-segregated polymer it was baked in air at 150° C. for 20 min. The PEDOT:PSS layer thickness was measured to be 40 nm.

Then an active 100-nm thick layer was spin-coated. The active layer was made of the porphyrin-(phenyl-perylene diimide)4-compound (TPP-PDI4) synthesized according to Example 1. The active layer was then coated with a thin film of LiF by thermal evaporation in vacuum. The aluminum contacts were deposited by thermal evaporation in vacuum as well. FIG. 29 shows the structure of prepared organic photovoltaic device comprising the glass substrate (19), the ITO-layer (20), the rectifying PEDOT:PSS-layer (21), the active layer made of the porphyrin-(phenyl-perylene diimide)4-compound (TPP-PDI4) (22), the rectifying LiF-layer (23), and aluminum contact layer (24).

What is claimed is:

1. A predominantly planar organic compound of the general structural formula I

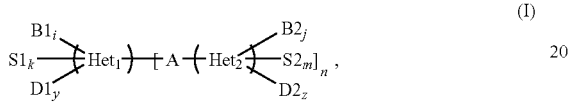

where $Het_1$ is a predominantly planar polycyclic molecular system of a first type;
$Het_2$ is a predominantly planar polycyclic molecular system of a second type;
A is a bridging group providing a lateral bond of the molecular system $Het_1$ with the molecular system $Het_2$ via strong chemical bonds;
n is 2, 3, 4, 5, 6, 7 or 8;
B1 and B2 are binding groups;
i is 0, 1, 2, 3, 4, 5, 6, 7 or 8;
j is 0, 1, 2, 3, 4, 5, 6, 7 or 8;
S1 and S2 are groups providing solubility of the organic compound;
k is 0, 1, 2, 3, 4, 5, 6, 7 or 8;
m is 0, 1, 2, 3, 4, 5, 6, 7 or 8;
wherein k+m≠0;
D1 and D2 are substituents independently selected from a list comprising —$CH_3$, —$C_2H_5$, $C_3H_7$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$;
y is 0, 1, 2, 3, 4, 5, 6, 7 or 8; and
z is 0, 1, 2, 3, 4, 5, 6, 7 or 8,
wherein said organic compound absorbs electromagnetic radiation in at least one predetermined spectral subrange within a wavelength range from 400 to 3000 nm and forms column-like or planar supramolecules;
wherein the molecular system $Het_1$, the bridging group A, and the molecular system $Het_2$ form a donor-bridge-acceptor system providing dissociation of excited electron-hole pairs; and a solution of the organic compound or its salt forms a solid photovoltaic layer on a substrate;
wherein at least one of the groups providing a solubility of the organic compound in organic solvents is independently selected from the list comprising alkyl, aryl, substituted alkyl, substituted aryl and any combination thereof, and amide of acid residue independently selected from the list comprising $CONR_1R_2$, CONH-$CONH_2$, $SO_2NR_1R_2$, and any combination thereof, where $R_1,R_2$ are independently selected from H, alkyl and aryl, and wherein the alkyl group is selected from methyl, ethyl, propyl, butyl, i-butyl and t-butyl groups, and the aryl group is selected from phenyl, benzyl and naphthyl groups,
wherein the column-like supramolecules are formed by means of π-π-interaction of single-type polycyclic molecular systems $Het_1$ and $Het_2$ providing separate hole and electron transport paths and having longitudinal axes oriented predominantly in the substrate plane predominantly parallel to each other and a number and a chain-length of the groups providing a solubility of the organic compound in organic solvent are selected to provide an electric isolation of the adjacent stacks of the column-like supramolecules; and
wherein planar supramolecules form molecular stacks by means of π-π-interaction of the single-type polycyclic molecular systems $Het_1$ and $Het_2$ providing different current-conducting-paths with electron and hole conductivity, wherein said molecular stacks are electrically isolated among themselves due to the groups providing solubility of the organic compound and the molecular stacks are oriented predominantly perpendicular to the substrate plane.

2. An organic compound according to claim 1, wherein at least one of the polycyclic molecular systems is a heterocyclic molecular system which comprises hetero-atoms selected from the list comprising nitrogen, oxygen, sulfur, and any combination thereof.

3. An organic compound according to claim 1, wherein the strong chemical bond is selected from the list comprising covalent bond, coordination bond, ionic bond, and any combination thereof.

4. An organic compound according to claim 1, wherein the predominantly planar polycyclic molecular system $Het_1$ and at least one predominantly planar polycyclic molecular system $Het_2$ absorb electromagnetic radiation in different predetermined spectral subranges within a wavelength range from 400 to 3000 nm.

5. An organic compound according to claim 1, wherein and at least one of the groups providing a solubility of the organic compound is independently selected from the list comprising the $COO^-$, $SO_3^-$, $HPO_3^-$, and $PO_3^{2-}$ and any combination thereof to provide solubility in water and/or water-miscible solvents.

6. An organic compound according to claim 1, wherein the groups providing a solubility of the organic compound provide solubility in an organic solvent selected from the list comprising benzene, toluene, xylenes, acetone, acetic acid, methyl ethyl ketone, hydrocarbons, chloroform, carbontetrachloride, methylenechloride, dichlorethane, chlorobenzene, alcohols, nitromethan, acetonitrile, dimethylforamide, 1,4-dioxane, tetrahydrofuran (THF), methylcyclohexane (MCH) and any combination thereof.

7. An organic compound according to claim 1, wherein i+j≥3 and the photovoltaic layer has planar supramolecules having polycyclic molecular systems with planes oriented predominantly parallel to the substrate plane due to lateral interaction of binding groups by means of strong and weak chemical bonds, wherein at least one of said planar supramolecules has the form selected from the list comprising disk, plate, lamella, ribbon and any combination thereof, wherein the strong chemical bond is selected from the list comprising covalent bond, coordination bond, ionic bond, and any combination thereof, and wherein said weak chemical bond is selected from the list comprising single hydrogen bond, dipole-dipole interaction, cation-π interaction, van der Waals interaction, π-π interaction, and any combination thereof.

8. An organic compound according to claim 1, wherein the predetermined spectral subrange is from 400 to 700 nm.

9. An organic compound according to claim 1, wherein at least one of the predominantly planar polycyclic molecular systems is partially or completely conjugated.

10. An organic compound according to claim 1, wherein at least one of the bridging groups is selected from the list comprising imidazole, perylene-3,4-dicarboximide, a series of p-phenylene (Php) oligomers, where p is 1, 2, 3, 4 or 5; and a series of 2,7-oligofluorene ($FL_S$) oligomers, where s is 1, 2, 3, or 4.

11. A predominantly planar organic compound of the general structural formula I,

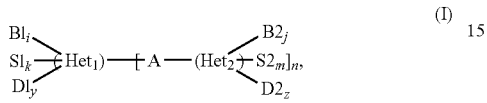

(I)

where $Het_1$ is a predominantly planar polycyclic molecular system of a first type;
$Het_2$ is a predominantly planar polycyclic molecular system of a second type;
A is a bridging group providing a lateral bond of the molecular system $Het_1$ with the molecular system $Het_2$ via strong chemical bonds;
n is 1, 2, 3, 4, 5, 6, 7 or 8;
B1 and B2 are binding groups;
i is 0, 1, 2, 3, 4, 5, 6, 7 or 8;
j is 0, 1, 2, 3, 4, 5, 6, 7 or 8;
S1 and S2 are groups providing solubility of the organic compound;
k is 0, 1, 2, 3, 4, 5, 6, 7 or 8;
m is 0, 1, 2, 3, 4, 5, 6, 7 or 8;
D1 and D2 are substituents independently selected from a list comprising —$CH_3$, —$C_2H_5$, $C_3H_7$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$;
y is 0, 1, 2, 3, 4, 5, 6, 7 or 8; and
z is 0, 1, 2, 3, 4, 5, 6, 7 or 8,
wherein said organic compound absorbs electromagnetic radiation in at least one predetermined spectral subrange within a wavelength range from 400 to 3000 nm and forms supramolecules;
wherein the molecular system $Het_1$, the bridging group A, and the molecular system $Het_2$ form a donor-bridge-acceptor system providing dissociation of excited electron-hole pairs; and a solution of the organic compound or its salt forms a solid photovoltaic layer on a substrate;
wherein i+j≠0 and at least one of the binding groups is an intra-binding group; and
wherein the intra-binding group is an alkyne-comprising group.

12. An organic compound according to claim 1, wherein i+j≠0, at least one of the binding groups is an inter-binding group, wherein at least one of the inter-binding groups is selected from the list comprising hetero-atoms, COOH, $SO_3H$, $H_2PO_3$, NH, $NH_2$, NHR, $NR_2$, and any combination thereof, where radical R is alkyl or aryl, and wherein the alkyl group is independently selected from methyl, ethyl, propyl, butyl, i-butyl and t-butyl groups, and the aryl group is selected from phenyl, benzyl and naphthyl groups.

13. An organic compound according to claim 1, wherein at least one of the predominantly planar polycyclic molecular systems $Het_1$ or $Het_2$ comprises tetrapirolic macro-cyclic fragments having a general structural formula from the group comprising structures 1-6, where Latin letter M denotes an atom of metal or two protons (2H):

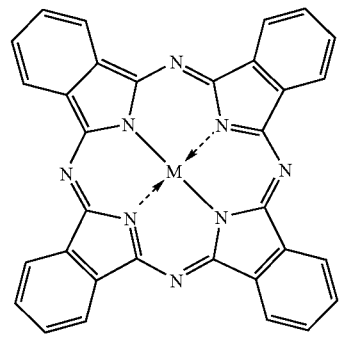

1

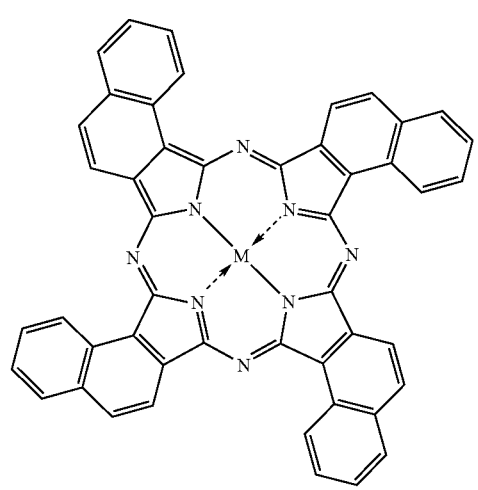

2

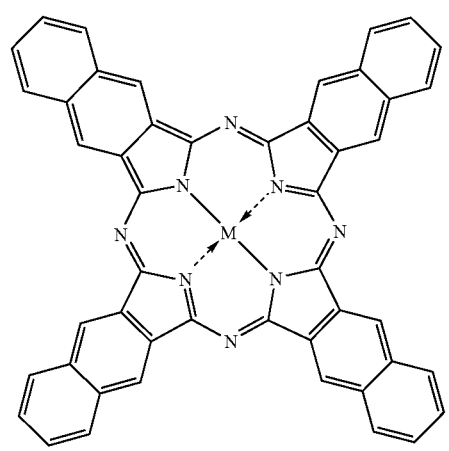

3

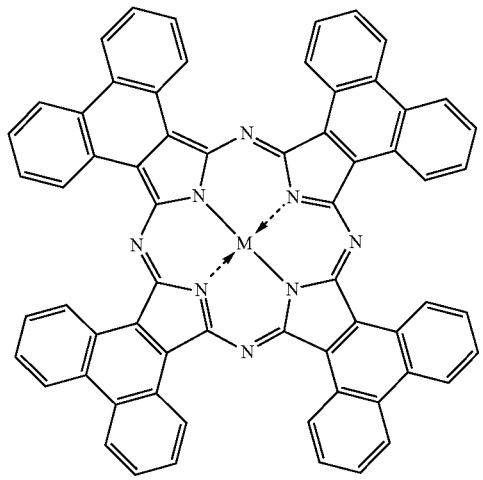
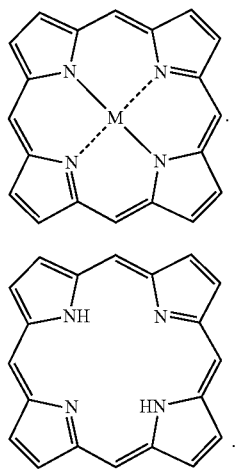
14. An organic compound according to claim 1, wherein at least one of the predominantly planar polycyclic molecular systems $Het_1$ or $Het_2$ comprises rylene fragments having the general structural formula from the group comprising structures 7-27:
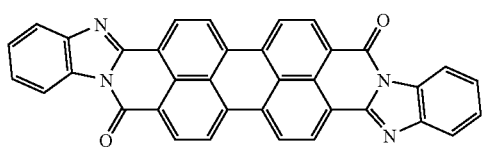
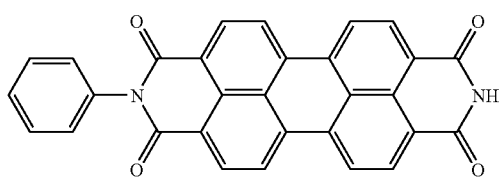
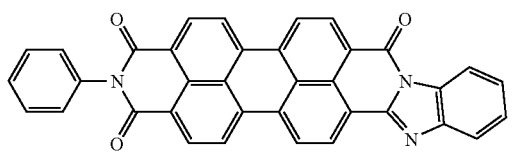
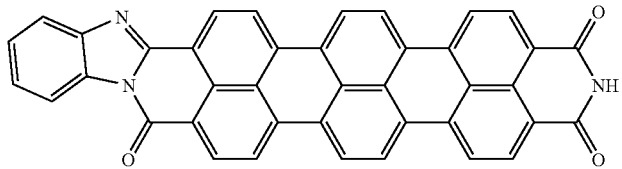
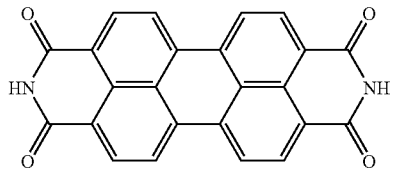

-continued
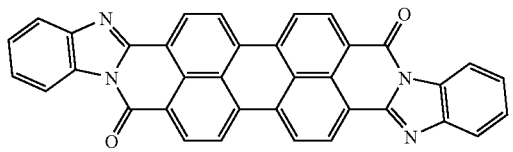
14
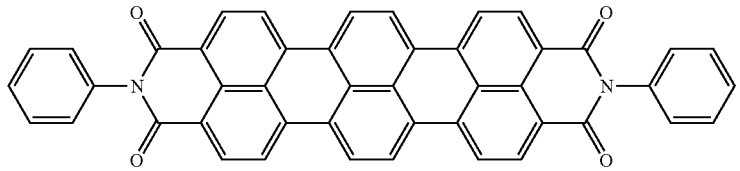
15
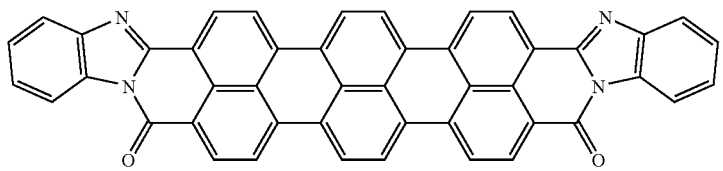
16
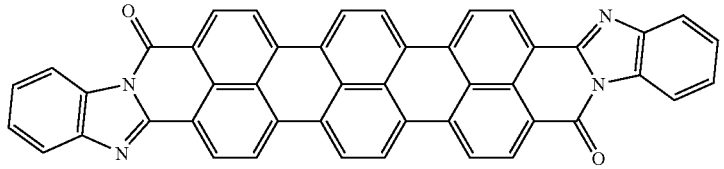
17
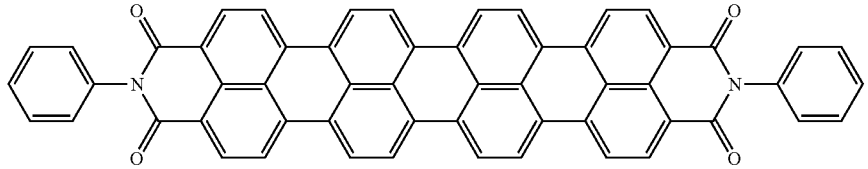
18
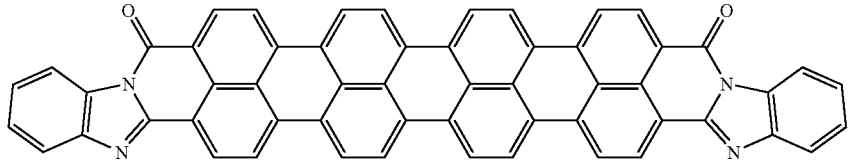
19
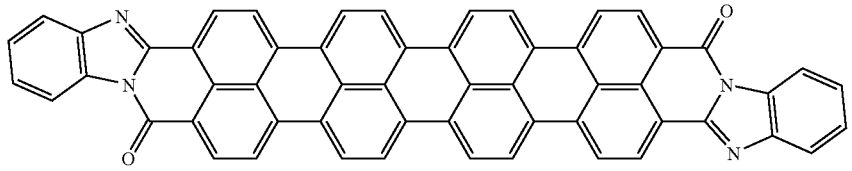
20
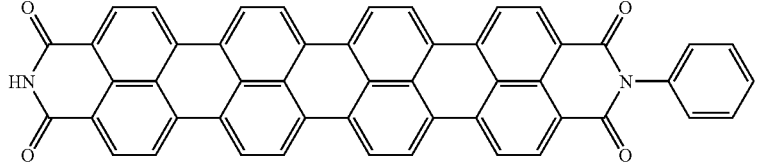
21
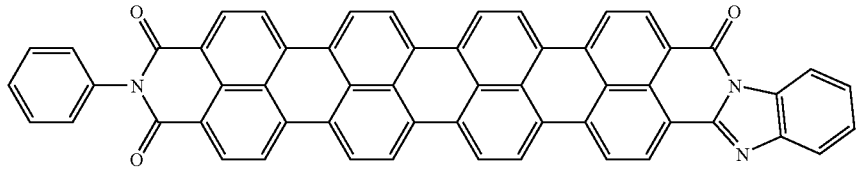
22

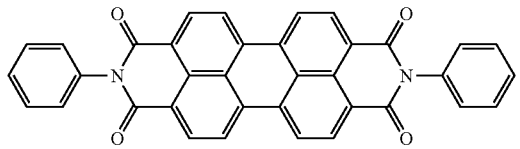

23

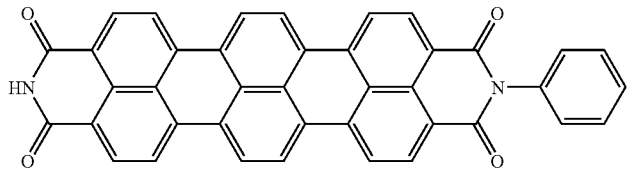 [SMILES: O=C1NC(=O)c2ccc3c4ccc5c6ccc7c8c(ccc(c9ccc(c%10ccc1c2c%103)c4c95)c86)C(=O)N(c1ccccc1)C7=O]

24

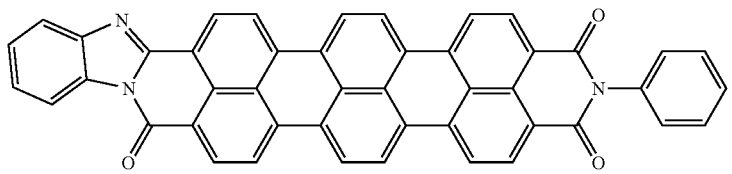 [SMILES: O=C1c2ccc3c4ccc5c6ccc7c(=O)n8c9ccccc9nc8c8ccc(c9ccc(c%10ccc(c2c3%10)C(=O)N1c1ccccc1)c4c59)c6c78]

25

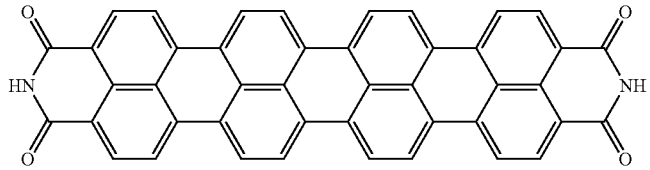 [SMILES: O=C1NC(=O)c2ccc3c4ccc5c6ccc7c8ccc9c%10c(ccc(c%11ccc(c%12ccc(c%13ccc1c2c%133)c4c%125)c6c%117)c%108)C(=O)NC9=O]

26

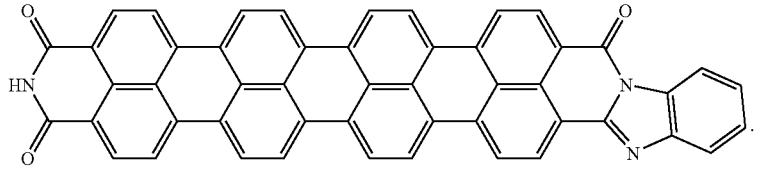

27

15. A predominantly planar organic compound of the general structural formula I,

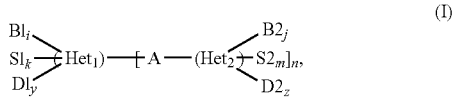

(I)

where $Het_1$ is a predominantly planar polycyclic molecular system of a first type;
$Het_2$ is a predominantly planar polycyclic molecular system of a second type;
A is a bridging group providing a lateral bond of the molecular system $Het_1$ with the molecular system $Het_2$ via strong chemical bonds;
n is 1, 2, 3, 4, 5, 6, 7 or 8;
B1 and B2 are binding groups;
i is 0, 1, 2, 3, 4, 5, 6, 7 or 8;
j is 0, 1, 2, 3, 4, 5, 6, 7 or 8;
S1 and S2 are groups providing solubility of the organic compound;
k is 0, 1, 2, 3, 4, 5, 6, 7 or 8;
m is 0, 1, 2, 3, 4, 5, 6, 7 or 8;
D1 and D2 are substituents independently selected from a list comprising —$CH_3$, —$C_2H_5$, $C_3H_7$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$;

y is 0, 1, 2, 3, 4, 5, 6, 7 or 8; and
z is 0, 1, 2, 3, 4, 5, 6, 7 or 8, wherein said organic compound absorbs electromagnetic radiation in at least one predetermined spectral subrange within a wavelength range from 400 to 3000 nm and forms supramolecules;

wherein the molecular system $Het_1$, the bridging group A, and the molecular system $Het_2$ form a donor-bridge-acceptor system providing dissociation of excited electron-hole pairs; and a solution of the organic compound or its salt forms a solid photovoltaic layer on a substrate;

and wherein at least one of the predominantly planar polycyclic molecular systems $Het_1$ or $Het_2$ comprises naphthalene fragments having the general structural formula from the group comprising structures 28-29:

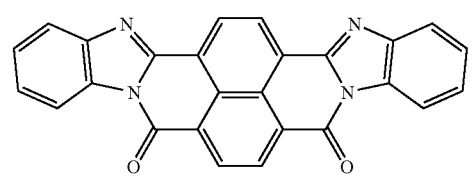 [SMILES: O=c1c2ccc3c(=O)n4c5ccccc5nc4c4ccc(c2c34)c2nc3ccccc3n12]

28

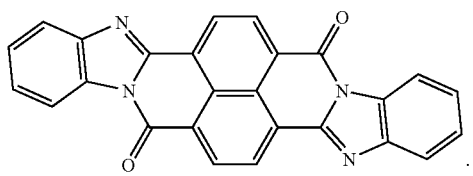

29

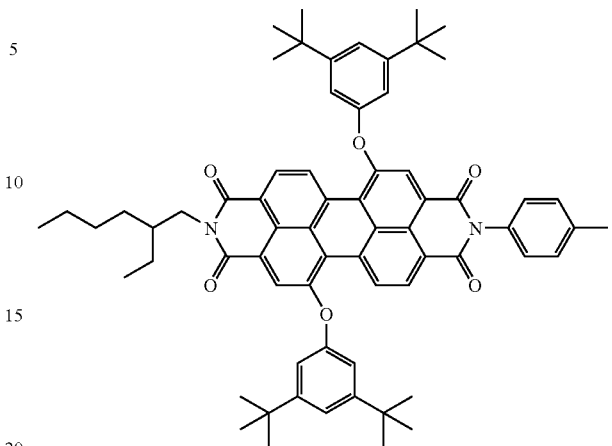

(III)

16. A predominantly planar organic compound of the general structural formula I,

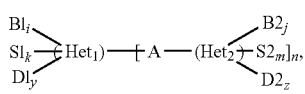

(I)

where $Het_1$ is a predominantly planar polycyclic molecular system of a first type;
$Het_2$ is a predominantly planar polycyclic molecular system of a second type;
A is a bridging group providing a lateral bond of the molecular system $Het_1$ with the molecular system $Het_2$ via strong chemical bonds;
n is 1, 2, 3, 4, 5, 6, 7 or 8;
B1 and B2 are binding groups;
i is 0, 1, 2, 3, 4, 5, 6, 7 or 8;
j is 0, 1, 2, 3, 4, 5, 6, 7 or 8;
S1 and S2 are groups providing solubility of the organic compound;
k is 0, 1, 2, 3, 4, 5, 6, 7 or 8;
m is 0, 1, 2, 3, 4, 5, 6, 7 or 8;
D1 and D2 are substituents independently selected from a list comprising —$CH_3$, —$C_2H_5$, $C_3H_7$, —$NO_2$, —Cl, —Br, —F, —$CF_3$, —CN, —OH, —$OCH_3$, —$OC_2H_5$, —$OCOCH_3$, —OCN, —SCN—$NH_2$, —$NHCOCH_3$, —$C_2Si(CH_3)_3$, and —$CONH_2$;
y is 0, 1, 2, 3, 4, 5, 6, 7 or 8; and
z is 0, 1, 2, 3, 4, 5, 6, 7 or 8,
wherein said organic compound absorbs electromagnetic radiation in at least one predetermined spectral subrange within a wavelength range from 400 to 3000 nm and forms supramolecules;
wherein the molecular system $Het_1$, the bridging group A, and the molecular system $Het_2$ form a donor-bridge-acceptor system providing dissociation of excited electron-hole pairs; and a solution of the organic compound or its salt forms a solid photovoltaic layer on a substrate; and
wherein the compound comprising fragments of the structural formula 6 as polycyclic molecular system Het1 and of the structural formula 9 as polycyclic molecular system Het2 and having a general structural formula III

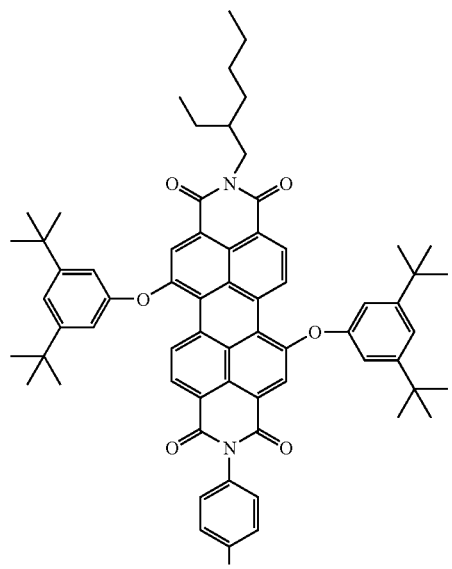

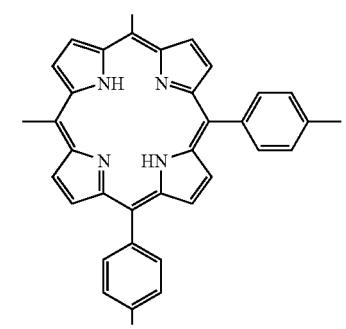

47
-continued
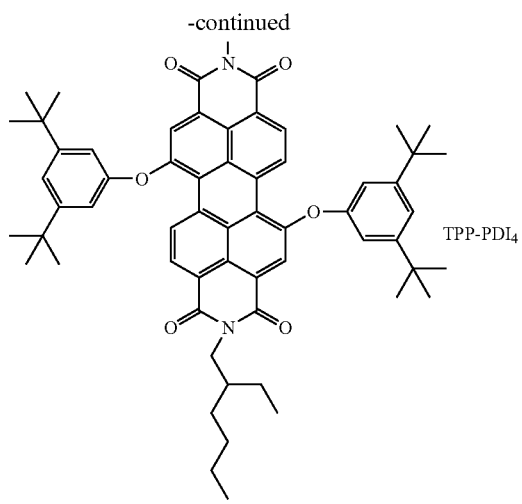
TPP-PDI4
48
-continued
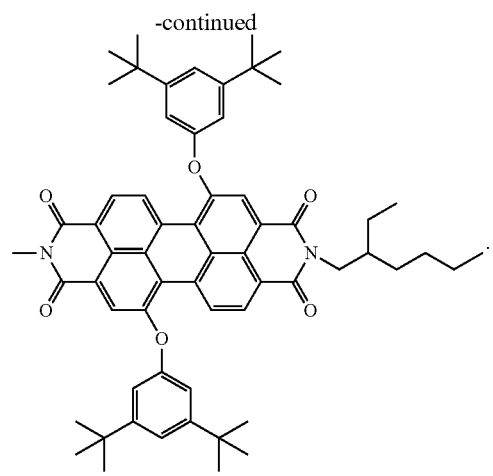
* * * * *